US012079704B1

(12) United States Patent
LaBorde

(10) Patent No.: US 12,079,704 B1
(45) Date of Patent: *Sep. 3, 2024

(54) SYSTEM, SERVER AND METHOD FOR PREDICTING ADVERSE EVENTS

(71) Applicant: Brain Trust Innovations I, LLC, Alpharetta, GA (US)

(72) Inventor: David LaBorde, Alpharetta, GA (US)

(73) Assignee: Brain Trust Innovations I, LLC, Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/051,510

(22) Filed: Oct. 31, 2022

Related U.S. Application Data

(63) Continuation of application No. 16/128,477, filed on Sep. 11, 2018, now Pat. No. 11,593,606.

(60) Provisional application No. 62/575,334, filed on Oct. 20, 2017.

(51) Int. Cl.
  *G06N 3/04* (2023.01)
  *G06K 19/07* (2006.01)
  *G06N 3/08* (2023.01)

(52) U.S. Cl.
  CPC ........... *G06N 3/04* (2013.01); *G06K 19/0723* (2013.01); *G06N 3/08* (2013.01)

(58) Field of Classification Search
  CPC .............. G06N 3/04; G06N 3/08; G06N 3/06; G06N 3/063; G06K 19/0723; G06K 19/07
  See application file for complete search history.

(56) References Cited

U.S. PATENT DOCUMENTS

| | | | |
|---|---|---|---|
| 7,158,030 B2 | 1/2007 | Chung | |
| 7,388,506 B2 | 6/2008 | Abbott | |
| 7,479,887 B2 | 1/2009 | Meyer | |
| 7,586,417 B2 | 9/2009 | Chisholm | |
| 7,772,981 B1 | 8/2010 | Lambert et al. | |
| 7,850,893 B2 | 12/2010 | Chisholm et al. | |
| 7,852,221 B2 | 12/2010 | Tuttle | |
| 7,875,227 B2 | 1/2011 | Chisholm | |
| 7,922,961 B2 | 4/2011 | Chisholm et al. | |
| 7,973,664 B1 | 7/2011 | Lambert et al. | |

(Continued)

OTHER PUBLICATIONS

Wallis et al., U.S. Appl. No. 62/531,250, "Systems and Methods for Predicting Multiple Healthcare Outcomes", filed Jul. 11, 2017, pp. 1-24, figures 1-6 (Year: 2017).*

(Continued)

*Primary Examiner* — Kamran Afshar
*Assistant Examiner* — Brian J Hales
(74) *Attorney, Agent, or Firm* — Culpepper IP, LLLC; Kerry S. Culpepper

(57) ABSTRACT

A system includes a data collection engine, a plurality of items including radio-frequency identification chips, a plurality of third party data and insight sources, a plurality of interfaces, client devices, a server and method thereof for preventing suicide. The server includes trained machine learning models, business logic and attributes of a plurality of patient events. The data collection engine sends attributes of new patient events to the server. The server can predict an adverse event risk of the new patient events based upon the attributes of the new patient events utilizing the trained machine learning models.

12 Claims, 28 Drawing Sheets

(56) References Cited

U.S. PATENT DOCUMENTS

| | | | |
|---|---|---|---|
| 8,005,767 B1* | 8/2011 | Cassella | G06V 10/763 |
| | | | 706/45 |
| 8,097,199 B2 | 1/2012 | Abbott et al. | |
| 8,098,162 B2 | 1/2012 | Abbott et al. | |
| 8,120,484 B2 | 2/2012 | Chisholm | |
| 8,181,875 B2 | 5/2012 | Nishido | |
| 8,212,226 B2 | 7/2012 | Chisholm | |
| 8,296,247 B2 | 10/2012 | Zhang et al. | |
| 8,478,535 B2 | 7/2013 | Jojic et al. | |
| 9,569,589 B1 | 2/2017 | LaBorde | |
| 9,679,108 B1 | 6/2017 | LaBorde | |
| 9,848,827 B1 | 12/2017 | LaBorde | |
| 9,928,342 B1 | 3/2018 | LaBorde | |
| 9,943,268 B1 | 4/2018 | LaBorde | |
| 9,977,865 B1 | 5/2018 | LaBorde | |
| 9,980,681 B1 | 5/2018 | LaBorde | |
| 10,014,076 B1 | 7/2018 | LaBorde | |
| 10,026,506 B1 | 7/2018 | LaBorde | |
| 10,028,707 B1 | 7/2018 | LaBorde | |
| 10,043,591 B1 | 8/2018 | LaBorde | |
| 10,043,592 B1 | 8/2018 | LaBorde | |
| 2010/0190436 A1 | 7/2010 | Cook et al. | |
| 2011/0291809 A1 | 12/2011 | Niemiec | |
| 2012/0095300 A1* | 4/2012 | McNair | G16H 50/30 |
| | | | 600/300 |
| 2013/0002034 A1 | 1/2013 | Onizuka et al. | |
| 2013/0246207 A1 | 9/2013 | Novak | |
| 2015/0213224 A1* | 7/2015 | Amarasingham | G16H 50/30 |
| | | | 705/2 |
| 2015/0317589 A1 | 11/2015 | Anderson et al. | |
| 2017/0370734 A1 | 12/2017 | Cojin | |
| 2018/0032690 A1 | 2/2018 | Perlman | |
| 2019/0019582 A1* | 1/2019 | Wallis | G06N 3/084 |

OTHER PUBLICATIONS

Frost, Steven A. and Tam, Victor and Alexandrou, Evan and Hunt, Leanne and Salamonson, Yenna and Davidson, Patricia M. and Parr, Michael J.A. and Hillman, Ken M. 2010. Readmission to intensive care: development of a nomogram for individualising risk. Critical Care and Resuscitation. 12 (2): pp. 83-89 (Year: 2010).*

Arthur et al., "Interhospital Transfer: An Independent Risk Factor for Mortality in the Surgical Intensive Care Unit," (2013), The American Surgeon, 79(9), 909-13 (Year: 2013).*

G. Nalini Priya and P. Anandha Kumar, "Neural network based efficient knowledge discovery in hospital databases using RFID technology," TENCON 2008—2008 IEEE Region 10 Conference, 2008, pp. 1-6, doi: 10.1109/TENCON.2008.4766474. With additional page to show online publication date (Year: 2008).*

Pivato et al., "Experimental Assessment of a RSS-based Localization Algorithm in Indoor Environment", [online], May 2010 [retrieved on Sep. 4, 2015]. Retrieved from the Internet: <URL:http://www.researchgate.net/profile/Paolo_Pivato/publication/224146714_Experimental_Assessment_of_a_RSS-based_Localization_Algorithm_in_Indoor_Environment/links/0912f502b6b29f22ea000000.pdf>.

Zafari et al., Micro-location for Internet of Things equipped Smart Buildings, [online], Jan. 7, 2015 [retrieved on Sep. 3, 2015]. Retrieved from the Internet:<URL:http://arxiv.org/abs/1501.01539>.

Bolic et al., "Proximity Detection with RFID: A Step Toward the Internet of Things", Apr. 23, 2015, Pervasive Computing IEEE, vol. 14 Issue:2, Published by IEEE.

Wong et al., "30 Years of Multidimensional Multivariate Visualization", [online], 1997 [retrieved on Aug. 12, 2016]. Retrieved from the Internet: <URL:http://citeseerx.ist.psu.edu/viewdoc/download?doi=10.1.1.30.4639&rep=rep1&type=pdf>.

Impinj, White Paper "New Thinking on an Old Challenge: Improving Healthcare Asset Management with Rain RFID Technology", [online], 2017 [retrieved on Nov. 16, 2017]. Retrieved from the Internet: <URL:https://www.impinj.com/media/2046/impinj-healthcare-asset-management-white-paper.pdf>.

Erica Drazen, "Using Tracking Tools to Improve Patient Flow in Hosptals", [online], Apr. 2011 [retrieved on Feb. 15, 2018]. Retrieved from the Internet: <URL:https://www.chcf.org/publication/using-tracking-tools-to-improve-patient-flow-in-hospitals/>.

Leaf Healthcare, White Paper "Technical Overview of the Leaf Patient Monitoring System", [online], 2018 [retrieved on Mar. 19, 2018]. Retrieved from the Internet: <URL:http://www.leafhealthcare.com/pdfs/LH_WP_TechOverview_1564AB_030818.pdf>.

Leaf Healthcare, "A New Standard for Optimizing Patient Repositioning", [online], 2018 [retrieved on Mar. 19, 2018]. Retrieved from the Internet: <URL:http://www.leafhealthcare.com/solution.cfm#s6>.

Suzanne Hodsden, "Smith & Nephew Integrates Wireless Patient Monitoring Into Wound Care Platform", Med Device Online, [online], Apr. 10, 2017 [retrieved on Mar. 19, 2018]. Retrieved from the Internet:<URL:https://www.meddeviceonline.com/doc/smith-nephew-integrates-wireless-patient-monitoring-into-wound-care-platform-0001>.

Robert R. Althoff, MD, PhD, "Suicide Risk Assessments in Hospitals Using Systematic Expert Risk Assessment for Suicide (SERAS)", [online], Jun. 5, 2018 [retrieved on Jul. 7, 2018]. Retrieved from the Internet: <URL: http://vtspc.org/wp-content/uploads/2018/06/Althoff-VT-Suicide-Prevention-Symposium-Presentation-6-4-18.pdf>.

Ann Grackin et al., "RFID Hardware: What You Must Know", RFID Technology Series, Jun. 2006.

Lyngsoe Systems, "PR34 X—Belt Loader RFID Reader User Guide", Apr. 16, 2016.

Lyngsoe Systems, "ADM User Manual", Sep. 21, 2010.

* cited by examiner

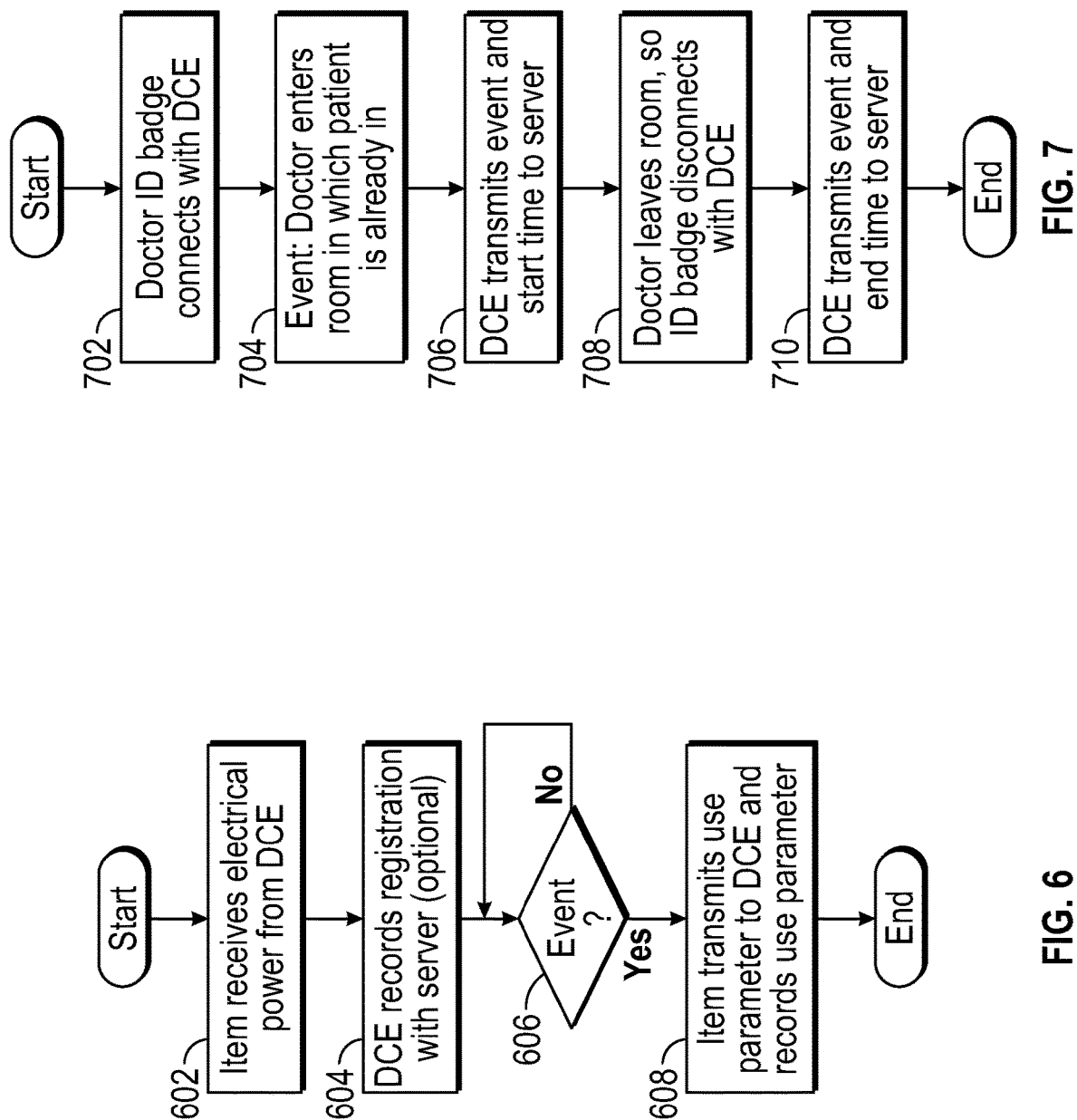

Data Fields/Properties

|  | Property 1 | Property 2 | Property 3 | ... | Property N |
|---|---|---|---|---|---|
| Data 1 |  |  |  |  |  |
| Data 2 |  |  |  |  |  |
| Data 3 |  |  |  |  |  |
| ... |  |  |  |  |  |
| Data N |  |  |  |  |  |

Collected Data

FIG. 15

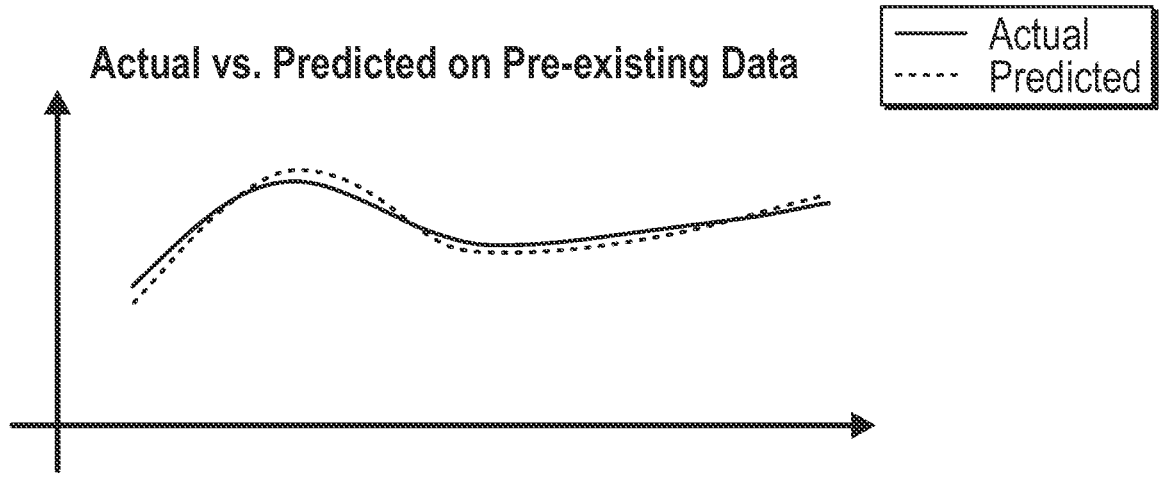
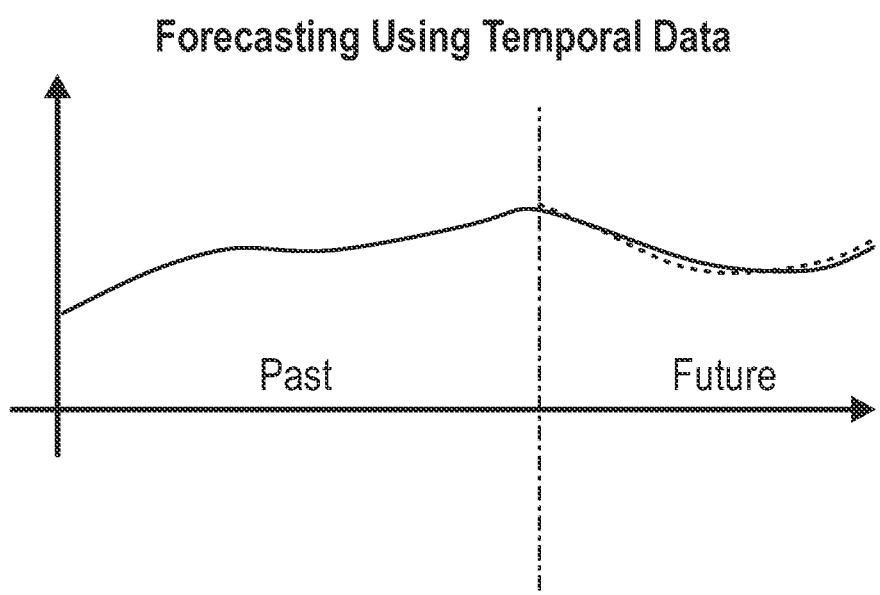
FIG. 21

SYSTEM, SERVER AND METHOD FOR PREDICTING ADVERSE EVENTS

CROSS-REFERENCE TO RELATED APPLICATIONS

The present application is a continuation of U.S. patent application Ser. No. 16/128,477 filed on Sep. 11, 2018, which claims the benefit of U.S. Provisional Patent Application No. 62/575,334 filed on Oct. 20, 2017, the contents all of which are incorporated herein by reference.

TECHNICAL FIELD

The technical field generally relates to a system including a client device, data input sources and a server device.

BACKGROUND

A radio-frequency Identification (RFID) chip can transmit information to a reader in response to an interrogation signal or polling request from the reader. The RFID chip can be incorporated in a tag (RFID tag) which is placed on a medical item such as a patient or doctor identification so that information can be passively captured. An RFID tag can be an active-type with its own power source, or a passive-type or battery-assisted passive type with no or limited power source. Both the passive-type and battery-assisted passive type will be referred to here as passive-type for sake of brevity. Placing an active-type RFID tag on some items may not be feasible due to financial considerations, weight, etc. On the other hand, placing a passive-type RFID tag on items may be more feasible; however, a power source will be needed to passively obtain information.

Artificial Intelligence (AI) technologies such as machine learning and deep learning have become ever present due to technological advances in data storage and processing. Machine learning at its most basic is the practice of using algorithms to parse data, learn from it, and then make a determination or prediction about something in the world. So rather than hand-coding software routines with a specific set of instructions to accomplish a particular task, the machine is "trained" using large amounts of data and algorithms that give it the ability to learn how to perform the task. Deep learning involves neural networks inspired by our understanding of the biology of our brains all those interconnections between the neurons. But, unlike a biological brain where any neuron can connect to any other neuron within a certain physical distance, these artificial neural networks have discrete layers, connections, and directions of data propagation.

SUMMARY

Medical care for patients is often provided among multiple providers across different facilities in a hospital system and in a plurality of care settings that may have no affiliation. The transfer of essential information and the responsibility for care of the patient from one health care provider to another is an integral component of communication in health care. This critical transfer point will be referred to herein as a handoff. It is very important to identify, diagnose and treat medical, operations, and administrative issues that may not be easily apparent during medical care to enable better care coordination, quality improvement, care surveillance, monitoring, and clinical business intelligence. However, this may be a challenge due to the multiple healthcare facilities and providers involved in the patient care.

A system that can identify which patient(s) within a ward full of patients are predicted to be at high risk for a preventable adverse event such as, for example, a medical error would be beneficial. It would be further beneficial if such a system can predict which specific adverse event is at high risk. With such a system, hospital leaders and managers can determine preventive intervention and obtain better situational awareness (i.e. alert on chart, hanging signs on door, higher level of unit/ward manager involvement/oversight, other, etc.).

Within a hospital facility or across a hospital system, a system that can identify which facilities and hospital areas (wards, operating rooms, procedure suites or areas, clinics, etc.) within specific facilities are predicted to have the highest rate of preventable adverse events per X number of admissions on an ongoing basis in real time would be beneficial. It would also be beneficial if the system could prioritize which facilities and areas within a given system most urgently need to undergo preventive intervention (i.e. personnel training on patient safety or change management intervention targeting the reduction of communication failures via the standardization of handoff and care transition processes).

The present disclosure concerns a system capable of leveraging AI techniques to identify patients at risk for adverse events and scenarios that may represent increased risk that an adverse event may occur. Moreover, the system enables the prediction of whether an adverse event may occur in particular location within a healthcare facility (predicted rate of medical errors per X admissions to Ward A or predicted rate of medical errors per X admissions with a primary diagnosis of Y to Ward A) and can provide a relative ranking of the respective risk across a variety of healthcare facilities within a healthcare system and across specific areas within a healthcare system (i.e. wards, operating rooms, procedure suites and/or areas, clinics, etc.).

The system can receive and deliver information to and from hospital information systems and client devices used by healthcare workers, patients, family members, and care givers. The system can include client devices for healthcare workers to manage their patients. The client devices can generate care coordination and administrative work flows, real time analytics, and data visualization tools that aid provider organizations and their healthcare worker employees in carrying out work flows, monitoring work flows and improving the quality and timeliness of the services delivered as a part of this work flow.

According to an aspect, the system comprises a plurality of input sources such as, for example, RFID tags, a reader device, a server device and a client device. The RFID tags can include active type and/or passive-type RFID tags. The reader device can be a data collection engine (DCE) device communicating with the RFID tags, wherein the DCE comprises: a power transmission subsystem including a power source and an antenna arranged to wirelessly transmit power from the power source to passive-type RFID tags; a transceiver configured to receive data including identification information from the RFID tags; a controller operatively coupled to the transceiver; and one or more memory sources operatively coupled to the controller including instructions for configuring the controller to generate one or more messages indicative of the identification information to be sent by the transceiver to a server device via the network connection. Each of the passive-type RFID tags includes an antenna for wirelessly receiving power from the transceiver of the DCE. The RFID tags include control logic for generating the identification information. The server device comprises: a transceiver configured to receive the one or more messages from the reader device; a controller operatively coupled to the transceiver; and one or more memory sources operatively coupled to the controller, the one or more memory sources storing a trained model for generating an output value corresponding to a present event based upon an input data set. The trained model can be a trained neural network model (NNM) or a trained self-organizing map (SOM).

The input data set can include identifications and locations of the patient and healthcare providers providing the patient care, handoffs and time intervals associated with the patient, etc. The output value can be a prediction of an adverse event.

The present disclosure further concerns a client device comprising: a transceiver communicating with the server device via a connection to a network, the transceiver configured to send a request message to the server device and receive a reply message from the server device in response to the request message, the reply message including an output value generated from the trained model stored at the server device; a controller coupled to the transceiver; a display device coupled to the controller; and a memory including instructions for configuring the controller to generate the request message and render a graphical display on the display device based upon the output value. The reply message can include a plurality of output values. The graphical display can include work flows that have been injected with predictive values from the trained models.

BRIEF DESCRIPTION OF THE DRAWINGS

The accompanying figures, in which like reference numerals refer to identical or functionally similar elements, together with the detailed description below are incorporated in and form part of the specification and serve to further illustrate various exemplary embodiments and explain various principles and advantages in accordance with the present invention.

FIG. 6-7 are flow diagrams illustrating exemplary operations of the system.

FIG. 15 is an illustration of an exemplary data set for patient attributes for various patient events.

FIG. 21 is an illustration of exemplary regression tasks performed by the client device.

DETAILED DESCRIPTION

In overview, the present disclosure concerns a system which includes various input data sources, client devices and backend devices. The input data source may include a Data Collection Engine (DCE) and RFID tags associated with, for example, identifications of medical professionals and patients. The backend devices can be one or more server devices.

The instant disclosure is provided to further explain in an enabling fashion the best modes of performing one or more embodiments. The disclosure is further offered to enhance an understanding and appreciation for the inventive principles and advantages thereof, rather than to limit in any manner. The invention is defined solely by the appended claims including any amendments made during the pendency of this application and all equivalents of those claims as issued.

It is further understood that the use of relational terms such as first and second, and the like, if any, are used solely to distinguish one from another entity, item, or action without necessarily requiring or implying any actual such relationship or order between such entities, items or actions. It is noted that some embodiments may include a plurality of processes or steps, which can be performed in any order, unless expressly and necessarily limited to a particular order; i.e., processes or steps that are not so limited may be performed in any order.

Reference will now be made in detail to the accompanying drawings. Wherever possible, the same reference numbers will be used throughout the drawings to refer to the same or like parts.

Figure 1:
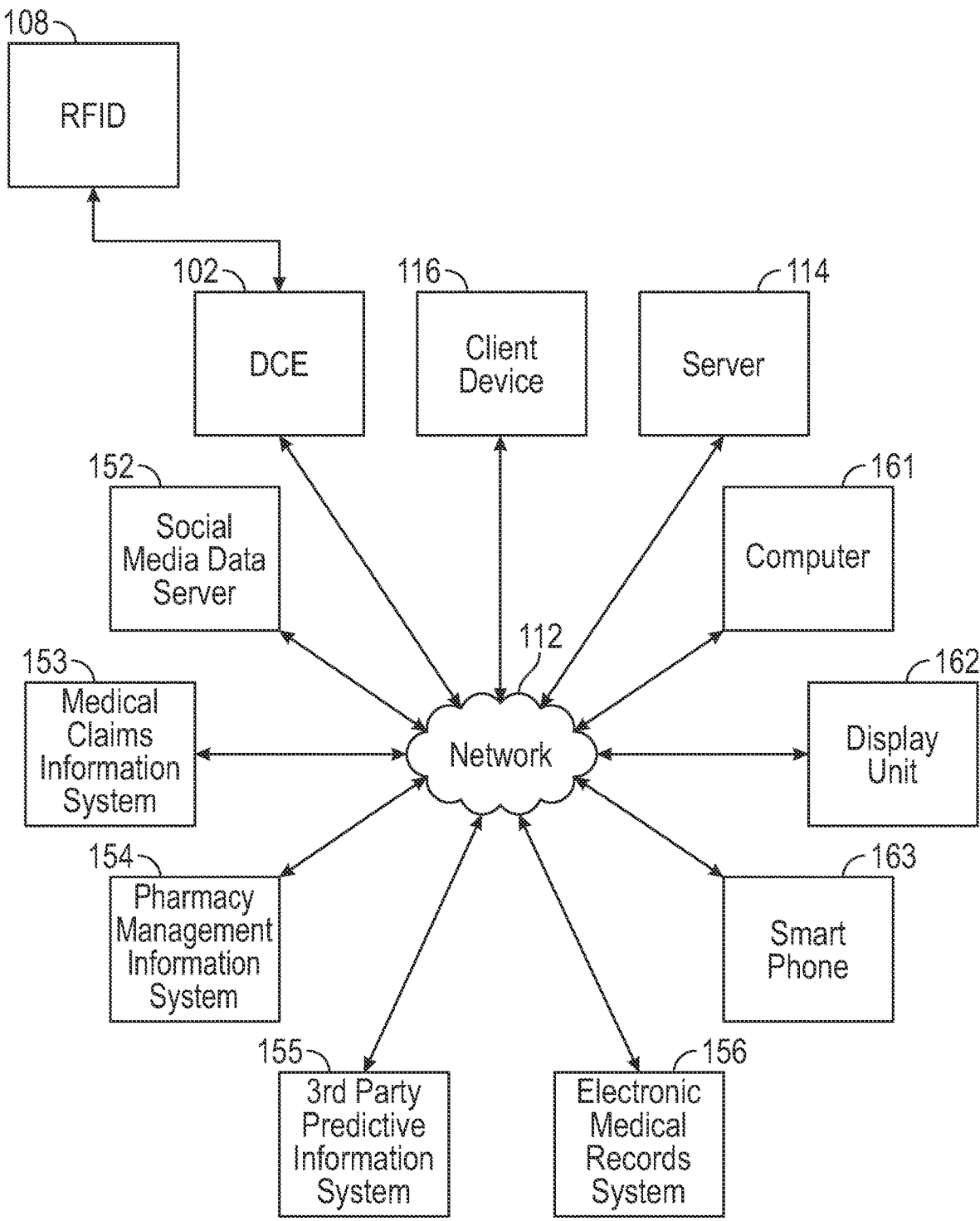
FIG. 1 illustrates an exemplary core operating environment in which the portions of the system communicate via a connection to a network.

Referring to FIG. 1, an exemplary operating environment in which the system, according to various embodiments, can be implemented will be discussed. The environment includes various input data sources such as a DCE 102, social media data server 152, medical claims information system 153, a pharmacy management information system data 154, third party predictive information system data 155, and an electronic medical records system data 156. The system is also capable of utilizing data originating from cameras, video sensors and even closed-circuit television and similar technologies in conjunction with facial recognition technology and facial expression analysis for emotion and behavior prediction as inputs into its predictive models. The system can also use various data inputs and changes therein over time.

Other example data sources not shown include: Hospital information systems; Scheduling system data; Adverse event reporting systems/databases; Joint Commission sentinel event reporting databases; Hospital specific safety reporting systems/databases; Incident reporting systems/databases; Morbidity and mortality systems/reports/databases; ICU safety reporting system; United Kingdom's National Patient Safety Agency maintains the National Reporting and Learning System; MEDMARX voluntary medication error reporting system; Hospital confidential event reporting systems; Root cause analyses; Employee, patient, family member feedback and survey data; Hospital Consumer Assessment of Healthcare Providers and Systems (HCAHPS); Patient facing software applications; Call centers; Law enforcement databases; Malpractice case law databases (i.e. Lexus Nexus, etc.); Community based medical centers via health information exchange (HIE) or other interfacing/data sharing approaches (i.e. HL7 Continuity of Care Documents, etc.); Consults for healthcare services (for example, medical or social services), status changes related to the fulfilment of consult requests, the content of consult requests and the reports received in response, and medical claims submitted for payment for services rendered in response to a consult; Imaging data (i.e. radiographically obtained imaging) and interpretations thereof (the findings); Laboratory data results; Vital sign observation results; Healthcare transportation records (i.e. ambulance, or other medical transport) and claims for payment remittance for such services; Data input from users (i.e. healthcare or administrative workers) that use client applications or that from 3rd party applications or systems; Known prior and future adverse events; Attributes describing patient's living situation (address, city, state, zip code); Economic data from the patient's location (i.e. unemployment rate, and other economic or other data); Attributes of the patient (i.e. married, single, race, body mass index, etc.); Data collected from care givers, family members and friends of the patient; Data collected from standardized patient assessments (i.e. SF-36); New articles/reports both video and print media, etc.

Figure 10:
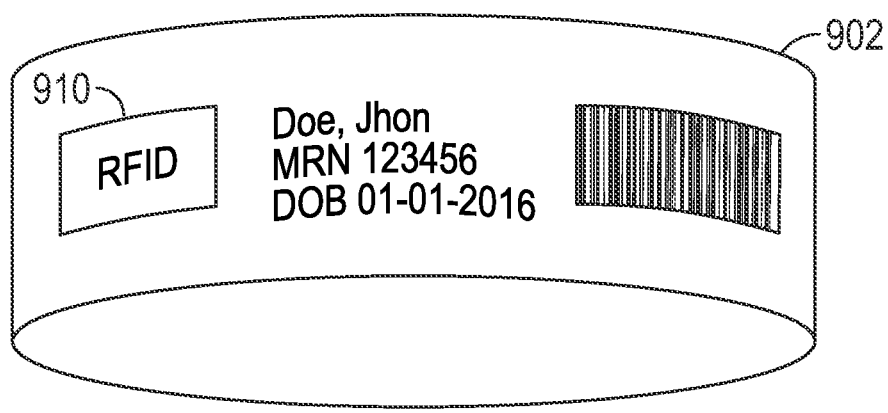
FIG. 10 is an illustration of a patient wrist band including an RFID tag.
Figure 11:
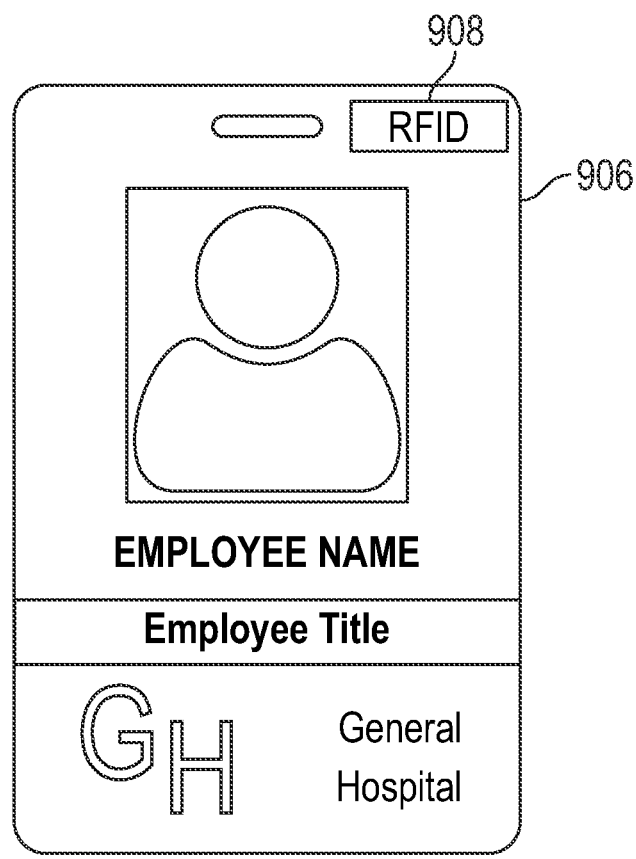
FIG. 11 is an illustration of a medical professional identification including an RFID tag.

The DCE 102 is shown communicating with an RFID tag 108. As discussed later, the DCE can be disposed in one or more rooms of a facility such as a hospital and the RFID tag 108 can be associated with a medical item such as a patient wrist band 902 (FIG. 10) or doctor ID badge 906 (FIG. 11). The communication between the RFID tag 108 and the DCE 102 is preferably wireless; however, wireline communication or a combination of wireless and wireline communication can also be used in some cases. Moreover, the system likely includes many DCEs. The DCE 102, as well as all of the data input sources, can communicate with one or more server devices (represented generally by and referred to hereon as "server") 114 via a connection to a network 112 such as a local area network (LAN), wide area network (WAN), the Internet, etc. A client device 116 can communicate with the server 114 and the DCE 102 via a connection to the network 112. Other computing devices such as computer 161, display unit 162 and smartphone 163 also communicate with the server 114 via the connection to the network 112. All communication can be encrypted or unencrypted. The network 112 can be, for example, a private LAN for the hospital facility. The server 114 can be a computing device local to the hospital facility. On the other hand, the network 112 can be the Internet, the DCE 102 can be local to the hospital facility and the server 114 can be one or more remote computing devices. The DCE 102 can be a reader device such as, for example, the TSL 1128. Handheld RAIN RFID reader made by IMPINJ™. One of ordinary skill in the art should appreciate that the server 114 can represent entities necessary for providing cloud computing such as infrastructure and service providers.

Figure 2:
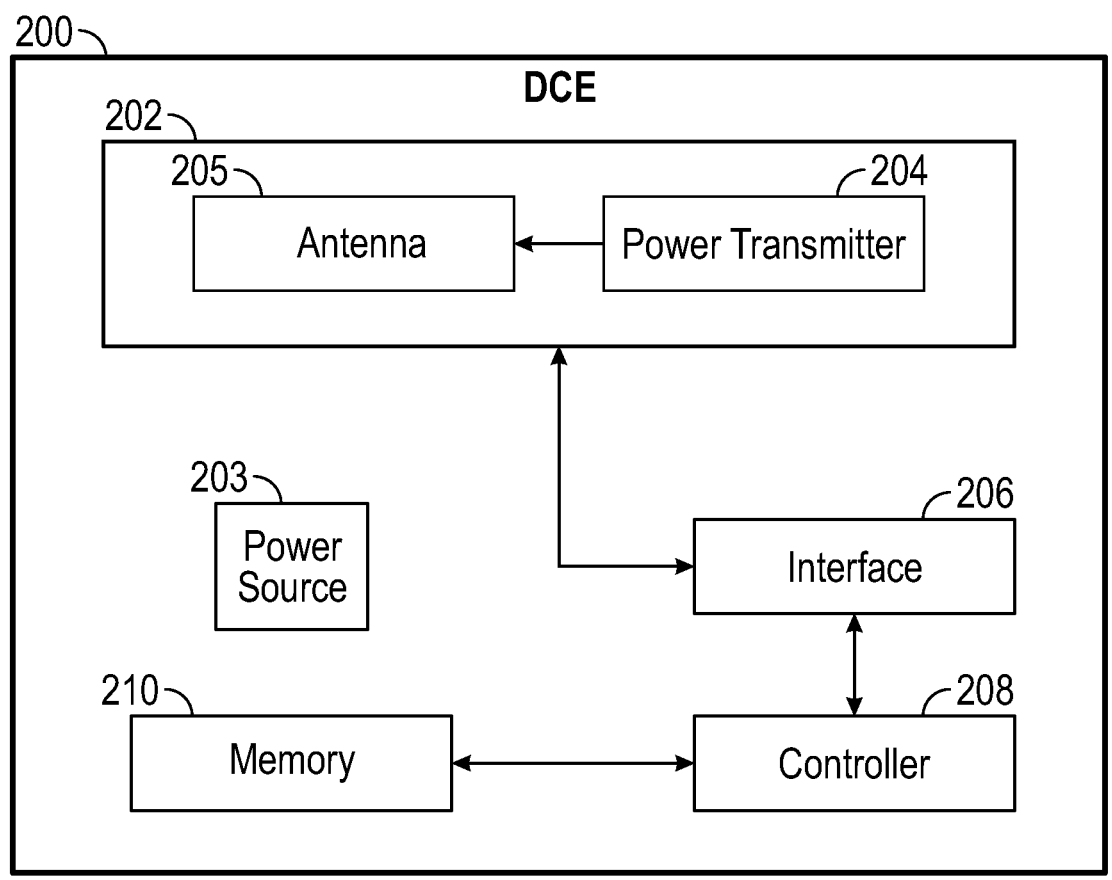
FIG. 2 is a block diagram illustrating exemplary portions of the DCE.

Referring to the block diagram of FIG. 2, portions of an exemplary DCE 200 will be discussed. The DCE 200 includes a transceiver 202, a power source 203, an interface 206, a controller 208 and one or more memory portions depicted by memory 210.

Referencing the Open Systems Interconnection reference model (OSI model), the transceiver 202 can provide the physical layer functions such as modulating packet bits into electromagnetic waves to be transmitted and demodulating received waves into packet bits to be processed by higher layers (at interface 206). The transceiver 202 can include an antenna portion 205, and radio technology circuitry such as, for example, ZigBee, Bluetooth and WiFi, as well as an Ethernet and a USB connection. The transceiver 202 also includes a wireless power transmitter 204 for generating a magnetic field or non-radiative field for providing energy transfer from the power source 203 and transmitting the energy to, for example, an RFID tag by antenna portion 205. The power transmitter 204 can include, for example, a power transmission coil. The antenna portion 205 can be, for example, a loop antenna which includes a ferrite core, capacitively loaded wire loops, multi-turn coils, etc. In addition to energy transfer, the transceiver portion 202 can also exchange data with the RFID tag. Data transmission can be done at, for example, 1.56 MHz. The data can be encoded according to, for example, Amplitude Shift Keying (ASK). The transceiver 202 includes a power transmission system composed of the antenna 205 and the power transmitter 204.

The interface 206 can provide the data link layer and network layer functions such as formatting packet bits to an appropriate format for transmission or received packet bits into an appropriate format for processing by the controller 208. For example, the interface 206 can be configured to encode or decode according to ASK. Further, the interface 206 can be configured in accordance with the 802.11 media access control (MAC) protocol and the TCP/IP protocol for data exchange with the server via a connection to the network. According to the MAC protocol, packet bits are encapsulated into frames for transmission and the encapsulation is removed from received frames. According to the TCP/IP protocol, error control is introduced and addressing is employed to ensure end-to-end delivery. Although shown separately here for simplicity, it should be noted that the interface 206 and the transceiver 202 may be implemented by a network interface consisting of a few integrated circuits.

The memory 210 can be a combination of a variety of types of memory such as random access memory (RAM), read only memory (ROM), flash memory, dynamic RAM (DRAM) or the like. The memory 210 can store location information and instructions for configuring the controller 208 to execute processes such as generating messages representative and indicative of data received from RFID tags as discussed more fully below.

The controller 208 can be a general purpose central processing unit (CPU) or an application specific integrated circuit (ASIC). For example, the controller 208 can be implemented by a 32 bit microcontroller. The controller 208 and the memory 210 can be part of a core (not shown).

In FIG. 1, the DCE 102 is shown communicating with RFID tag 108. However, other devices such as smartphone 163, for example, can also communicate with the RFID tag.

Figure 3A:
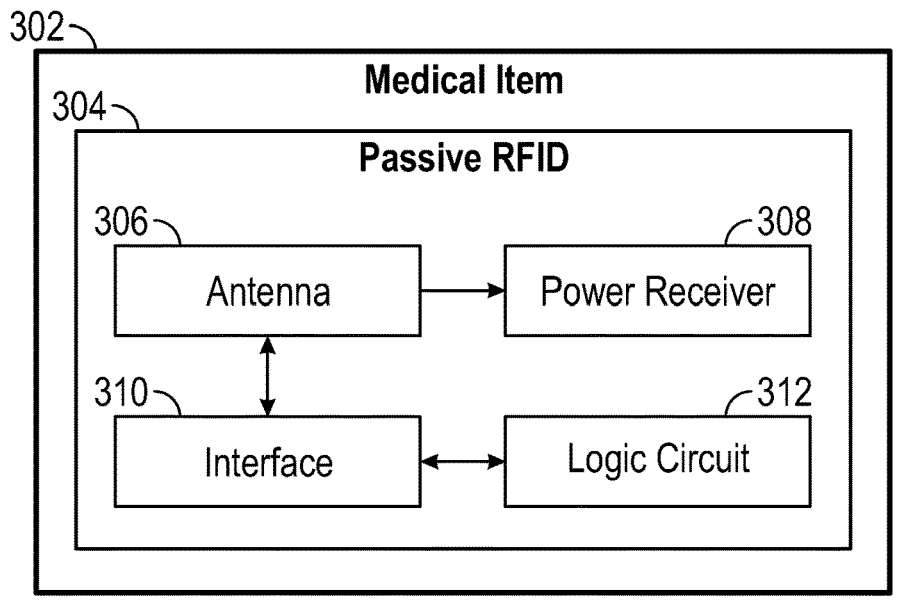
FIG. 3A is a block diagram illustrating exemplary portions of a passive-type RFID tag.

Referring to FIG. 3A, portions of an exemplary passive-type RFID tag 304 on a medical item 302 will be discussed. The RFID tag 304 can include an antenna portion 306, a power receiver 308, an interface 310 and a logic circuit 312. The antenna portion 306 can be a loop antenna which includes a ferrite core, capacitively loaded wire loops, multi-turn coils, etc., similar to the antenna portion 205 of the DCE 200. The power receiver 308 can include a power receiving coil for receiving power from the power transmission coil of the power transmitter 204 by electromagnetic coupling. The power receiver 308 can provide power to the chip 304 and/or charge a power source (not shown) such as a battery.

Generally, the logic circuit 312 generates data such as an identification of the RFID tag and/or the item to which it is affixed, state, location, and changes in any data or properties thereof over time, all of which will be referred to as medical data. It should be noted that the data includes situational data which refers to a) the identity of the RFID tag, the identity reference for an individual, facility, property, equipment to which the RFID tag is affixed, and b) the distance between an RFID tag and other RFID tags, the distance between the RFID tag and the DCE, the distance between the RFID and a client device such as smartphone, the identity and any identity references of the other RFID tags, DCEs and mobile client devices (i.e. smartphones) with which the RFID communicates, and any obtained from a sensor associated with i) the RFID tag or ii) another RFID tag, or client device (i.e. smartphone) with which the RFID communicates. Examples of the sensor data might be location in three dimensions, acceleration or velocity, displacement relative to some reference, temperature, pressure, to name a few.

The data can also include data indicative of an event such as, for example, near field communication (NFC) established with the DCE or another RFID tag, a time duration for which the RFID tag 304 has been within a certain location, historical data, etc. Although not shown, the logic circuit 312 can include or be coupled to a non-volatile memory or other memory sources.

The interface 310 can format a received signal into an appropriate format for processing by the logic circuit 312 or can format the medical data received from the logic circuit 312 into an appropriate format for transmission. For example, the interface 310 can demodulate ASK signals or modulate data from the logic circuit 312 into ASK signals.

Figure 3B:
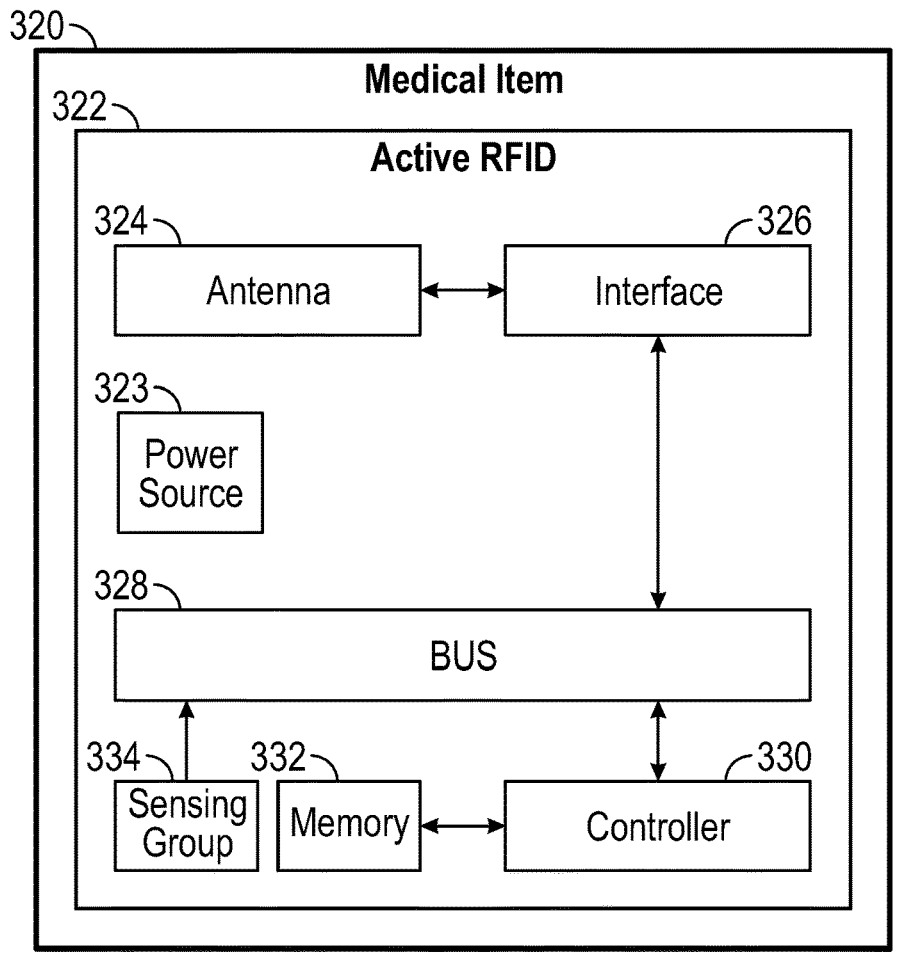
FIG. 3B is a block diagram illustrating exemplary portions of an active-type RFID tag.

Referring to FIG. 3B, circuit-level portions of the active-type RFID tag 322 on a medical item 320 will be discussed. The RFID tag 322 can include a power source 323, an antenna portion 324, an interface 326, a bus 328, a controller 330, a memory portion 332 and a sensing group 334. The power source 323 can be, for example, a battery. Although not shown, the tag 322 can also include a power management portion coupled to the power source 323.

The antenna portion 324 and interface 326 can be similar to those of the passive-type RFID tag 304. However, it should be noted that the antenna portion 324 can receive data from other passive-type and active-type RFID tags as well as the DCE and can send this and other data to the DCE, or other RFID tags.

The sensing group 334 includes sensing portions for sensing contact, motion characteristics such as an acceleration value, whether the tag is within a predetermined distance from another RFID tag, a distance from one or more other RFID tags and/or the DCE, and/or distance and angle from a baseline orientation. The sensing group 334 can include a set of accelerometers for determining the acceleration value of the item 320, a digital compass that collects orientation information about the item 320, a gyroscope for measuring angular rotation associated with the apparatus to provide an orientation value, a proximity sensor for detecting if the chip 322 is within a predetermined distance of another chip 322, a touch sensor layer and/or pressure sensor for sensing contact and magnitude of the pressure, and a geomagnetic sensor for sensing geomagnetic field strength. Preferably, the sensed motion characteristics include data represented in the time domain. The accelerometers can detect subtle movements along the three axial directions. The accelerometer reading, when combined with the data from the digital compass and/or the gyroscope, can facilitate motion detection. The sensing group 334 can include a separate OpenBeacon active tag or a Sense-a-Tag as described in "Proximity Detection with RFID: A Step Toward the Internet of Things" by Bolić et al., Pervasive Computing, IEEE, (Volume 14, Issue 2), published on April-June 2015, the contents of which are incorporated herein by reference. Further, in conjunction with or separately from the proximity sensor, the sensing group can include a distance sensor for measuring a distance to a target node such as another RFID chip. The distance sensor may be a received signal strength (RSS) indicator type sensor for measuring the RSS of a signal received from a target node such as the DCE or another RFID chip. The distance from the target node can be obtained by a plurality of RSS measurements.

The controller 330 is configured according to instructions in the memory 332 to generate messages to be sent to the DCE or another tag. Particularly, the controller 330 can be configured to send a registration message which includes identification data associated with the RFID tag 322 and thus the item 320. Further, in a case in which the RFID tag 322 wirelessly provides power to another passive-type RFID tag, the controller 330 can be configured to generate a message including identification data associated with the passive-type RFID tag, in combination with, or separately from its own identification data to the DCE.

The controller 330 can be configured to generate messages including data indicative of an event. These types of messages can be sent upon receiving a request from the DCE or another entity, upon occurrence of the event, or at regular intervals. Example events include near field communication established with another RFID tag, contact detected by the sensing group 334, positional information, a time duration of such contact and position, etc.

It should be noted that the passive-type RFID tag can also include a sensing group or be coupled to the sensing group. For example, the RFID tag 304 can be a Vortex passive RFID sensor tag which includes a LPS331AP pressure sensor or a MONZA X-8K DURA or X-2K DURA tag made by IMPINJ™ which includes embedded sensors. Both active and passive types of sensors can include RSS measurement indicators. The controller or control logic can determine the distance from the RSS measurements based upon localization algorithms such as, for example, Centroid Location (CL), Weighted CL, or the Relative Span Exponentially Weighted Localization (REWL) algorithm as discussed in "Experimental Assessment of a RSS-based Localization Algorithm in Indoor Environment" by Pivato et al., IEEE Instrumentation and Measurement Technology Conference, published on May 2010, the contents of which are incorporated herein by reference. As mentioned above, the DCE 102 can store data regarding its fixed location (i.e. room). In this case, the physical location of the RFID tag 110 can be determined via the DCE 102. Alternatively, the RFID tags can obtain position from some external reference (i.e. a device with GPS or via a device that provides an indoor positioning system location reference, or WiFi hotspots, that themselves have a known location, which can somehow transmit WiFi ids to the RFID chips). This later approach, involving an external device other than the DCE 102, would occur via having the other external device communicate with the RFID tag and write location data to the RFID tag memory which is then sent along with any messages to the DCE. Further, the RFID tags could also be designed to record this location information from an external source upon being interrogated by a DCE.

Figure 4:
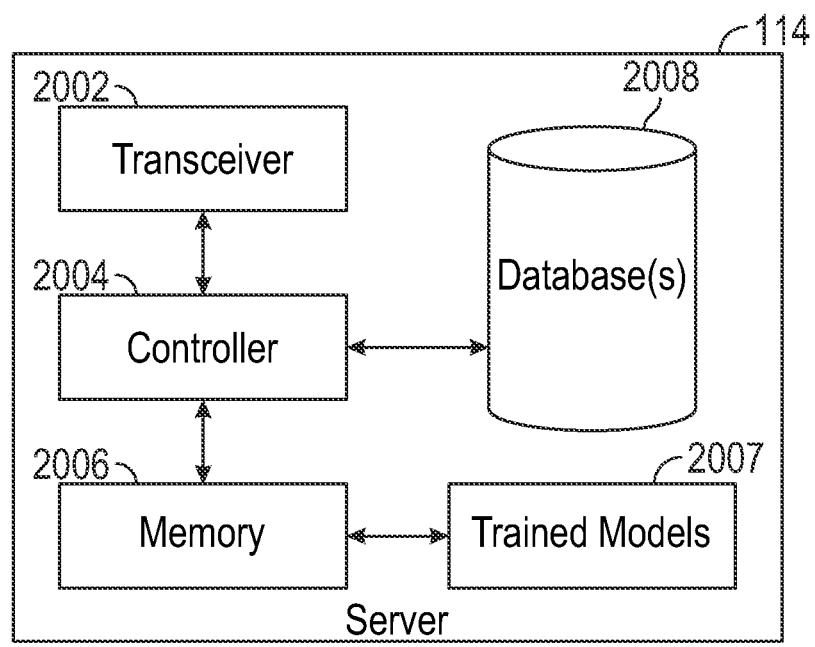
FIG. 4 is a block diagram illustrating exemplary portions of a server device according to an embodiment.

Referring to FIG. 4, the server 114 includes a transceiver 2002, a controller 2004, a first memory portion 2006, a second memory portion 2007 and one or more databases stored in another memory source depicted generally by database 2008. The transceiver 2002 can be similar to the transceiver of the DCE. The transceiver 2002 receives data via the network from the DCE, data retrieval requests from the client device 116 and sends replies to the data retrieval requests. The databases 2008 can include an item database, a patient database, and a medical professional database. That database can be, for example, an atomic data store. The transceiver 2002 receives data via the network from the DCE and resource requests such as, for example, http requests, via the network, from a client device. The resource request can include verification credentials such as a token issued from a certification authority and a user name and an information request for an information reply including usage parameters associated with one or more RFID chips. The transceiver 2002 sends the information reply including the usage parameters associated with the one or more RFID chips to the client device. The transceiver 2002 can be similar to the transceiver of the DCE.

The memory portions 2006, 2007, 2008 can be one or a combination of a variety of types of memory such as RAM, ROM, flash memory, DRAM or the like. The memory portion 2006 includes instructions for configuring the controller 2004. The second memory portion 2007 includes one or more trained models. It should be noted that the database and the trained models can be included in the memory portion 2006. They are shown separately here in order to facilitate discussion. The data inputs as discussed above are collectively stored the database 2008.

The controller 2004 is configured according to the instructions in the first memory portion 2006 to determine data in the database 2008 that is associated with the identification for each of the one or more RFID tags (received in the message from the DCE); store data in the message from the DCE in the database 2008 to be associated with the identification of the first RFID tag; and as will be discussed more fully below, predict an adverse risk associated with a patient event based upon inputting attributes of the patient event into the trained model such as a neural network model or self-organizing map network.

The controller 2004 and database 2008 can be configured to perform command query responsibility segregation in which commands are separated from queries to allow scaling of servers that respond to queries separately from servers delegated to responding to messages. The controller 2004 and database 2008 can further be configured to use event sourcing and/or event streaming to ensure all changes to an application state get stored as a series of events which can be not only queried but reconstructed.

Figure 5:
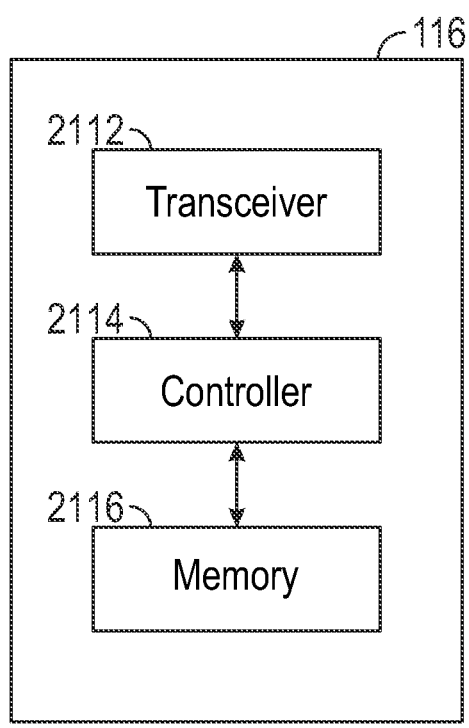
FIG. 5 is a block diagram illustrating exemplary portions of a client device.
Figure 8:
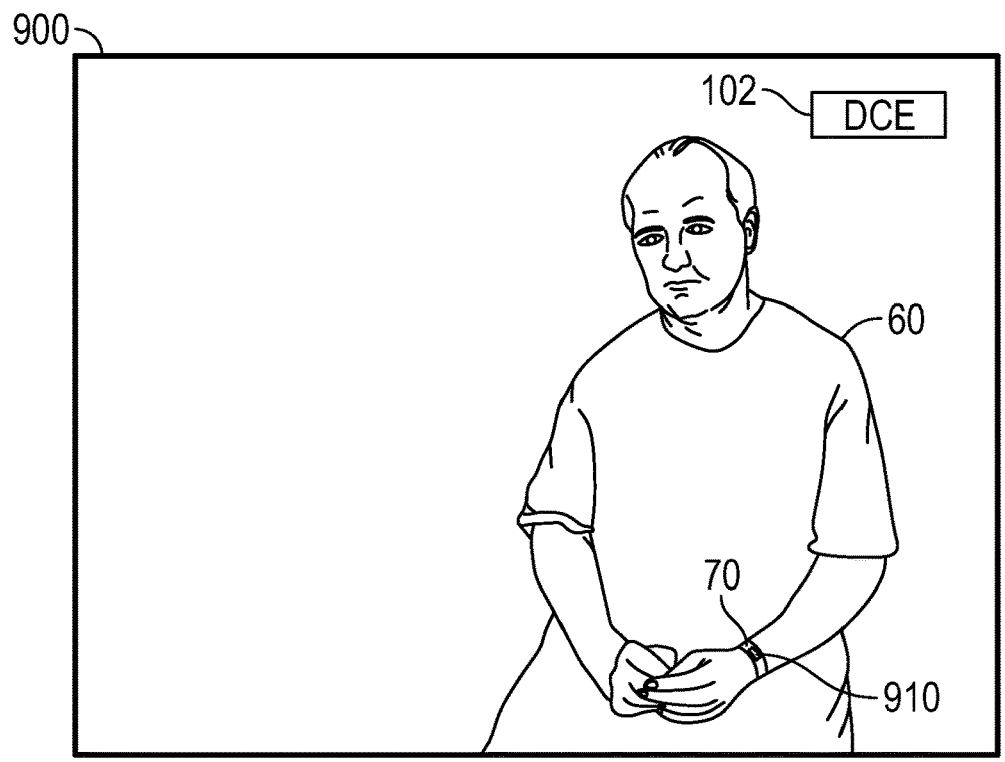
FIG. 8 is an illustration of an exemplary patient wearing a patient identification band with a RFID tag.

Referring to FIG. 5, the client device 116 includes a transceiver 2112, a controller 2114 and memory 2116. The transceiver 2112 can be similar to the transceiver of the DCE. The transceiver 2112 sends an information request message generated by the controller 2114 to the server device 114. The request can include verification credentials such as a token issued from a certification authority (which must be determined to be valid and to contain the requisite claims for the resource being requested in order for the request to be successfully processed), and a user identifier and an information request for calculated quantifiable outcomes for a plurality of patient events. The transceiver receives receives a reply message from the server device in response to the request message, the reply message including an output value generated from the trained model stored at the server device. The controller 2114 is configured according to instructions in the memory 2116 to generate visualization data (i.e. a json object) or graphical displays (i.e. html markup and javascript) including visualization data on a display on the client device based upon the output value. For example, the graphical display can indicate a predicted risk of medical error.

It should be noted that portions of server 114 may be distributed among various computing devices. For example, the trained models shown stored in memory portion 2007 or the database(s) 2008 could be stored at a plurality of different computing devices. Modifications as described above and below to the embodiments may be combined and are not limiting to the inventive system.

Besides the RFID tags, the server 114 can receive input data from work flows associated with client devices used in the process of managing patients as well as data derived from activity tracked via the hospital information systems; some examples of the latter include appointments, patient movements, facility visits or admissions, healthcare employee charting, among others.

Some examples of data the system collects and leverages include: i) any patient record flags from hospital medical records and any reviews thereof, renewals, discontinuations and related documentation, for example documentation explaining the basis for continuance or discontinuation; ii) healthcare or social services worker charting including, but not limited to social worker charting, physician and psychologist charting, handover plans and risk assessments and other charting including, but not limited to: a) metadata about the charting such as note title, date of creation, date signed by author or cosigners, identity of author and any cosigners; and b) content of such charting both structured and free text; iii) any appointments the patient has scheduled for medical or social services; iv) hospital information system registration and patient movement data from medical facilities, both the local facility and remote facilities via healthcare information exchange. Utilizing proprietary business logic and analytics, the system can identify situations that may represent a change or increase in the risk of an adverse event and when such scenarios are identified, escalate this concern to the appropriate stakeholders.

Authentication and Authorization

Access to the system is secure and requires authentication and authorization and data communications are encrypted. The system's end user functionality can be accessed via desktop workstation or mobile device and can be via the system's client applications running in a web browser or via the system's native applications running on a mobile or desktop device. The system's user interfaces adapt to a variety of device form factors and viewport sizes.

The system and its related client applications have the ability to encrypt and decrypt data as needed to execute necessary business processes and logic and for presentation of data to authenticated and authorized users in the user interfaces of the systems client applications.

Access to the system's client application-based workflow and communications solutions and dashboard and data visualization technologies is controlled using state of the art access control technologies via which users are authenticated and authorized, for example, OAuth2/claims based security, OpenIdConnect, etc. The system also can be configured to use enterprise access control systems, for example, but not limited to, Lightweight Directory Access Protocol (LDAP), the Department of Veterans Affairs Citrix Access Gateway (CAG), Personal Identity Verification (PIV) Card, and/or Access/Verify based authorization/authentication. In addition, the system can be configured to work with single sign on technologies.

Data sent and received by the system is encrypted in motion and at rest and can be configured to use current and future state of the art encryption methodologies such as Triple Data Encryption Standard (DES), the Rivest-Shamir-Adleman (RSA) cryptosystem, Blowfish, Two Fish, Advanced Encryption Standard (AES), among others.

Data Visualization and Client Application

The system provides data visualization technologies, briefly described above, to enable its users to observe trends, easily assess the current status of particular processes or work flows versus targets/thresholds/reference ranges, all in real time. The system utilizes business rules, graphics, charts, the visual presentation of statistical process control analytics, icons, animation, color and text to highlight particular information. The dashboard makes current trends available and provides inputs and controls that enable "drill down/roll up" and "slice and dice" features that leverage attributes of the input data and metrics; this provides ad hoc query functionality that allows end users to examine data, metrics, and key performance indicators in aggregate, and/or for particular sub groups over configurable date ranges. The system can be configured to send out, for example via email, periodic reports that detail performance and trends over time. For example, multiple teams of healthcare workers at a given facility or across multiple facilities may be tasked with managing particular patients at high risk for an adverse event. The system's work flow tools and analytics in conjunction with end user configuration can determine which teams and individuals are responsible for managing the care of a given patient at high risk for an adverse event. Leveraging this knowledge, the system provides proprietary scoring of performance in aggregate, for each team, and for each individual. Because particular aspects of the system's proprietary technology enabled monitoring of specific work flows assesses and tracks activities that are initiated and carried out by humans, such as healthcare or social services workers, these attributes and objective observations made by the system on each patient's care as carried out by human actors can be input into the inventive systems predictive analytics and proprietary scoring algorithms. Scores generated from these proprietary algorithms can, of course be used in predicting the risk for an adverse event, but also can be used to provide aggregate, subgroup and individual performance data over particular date ranges and at various snapshots in time enabling healthcare provider organizations, managers, and facility leaders to monitor processes in real time and over time and improve performance/maximize the effectiveness of their efforts to prevent adverse events.

First Embodiment

As described more fully below, the system leverages proprietary models that are trained, for example, using supervised machine learning to determine whether a patient that has or has not been handed off during a given interval of time has had a change (for example a worsening) in the predicted risk of an adverse event. For example, using a simple, human understandable example, if a certain interval of time elapses and a patient has or has not been handed off one or more times by various disciplines (admitting team, consulting team, nursing) within a given window of time (during which the system knows the on-duty personnel has changed one or more times) as determined by RFID data captured by the DCE, workflow data capture, and documentation the server ingests and analyzes, the trained model would be used to assess whether the pattern of events (or lack thereof) in the context of other data the system has access leads to a significant increase in the individuals predicted risk for a preventable medical error or adverse event.

Referring to FIGS. 6-13, a first embodiment will be discussed by exemplary cases in which the DCE 102 receives data from the RFID tag. In the case shown in FIG. 8, the DCE 102 is located at medical facility room 900. A Patient ID badge 70 including an RFID tag (passive or active) 910 is worn by a patient 60. The DCE 102 establishes communication with the RFID tag 910. Particularly, the DCE 102 can periodically generate a broadcast message, and receive a registration message including identification data from the RFID tag 910 in reply to the broadcast message. Alternatively, the RFID tag 910 can self-initiate sending of the registration message periodically or in response to another external trigger.

Figure 9:
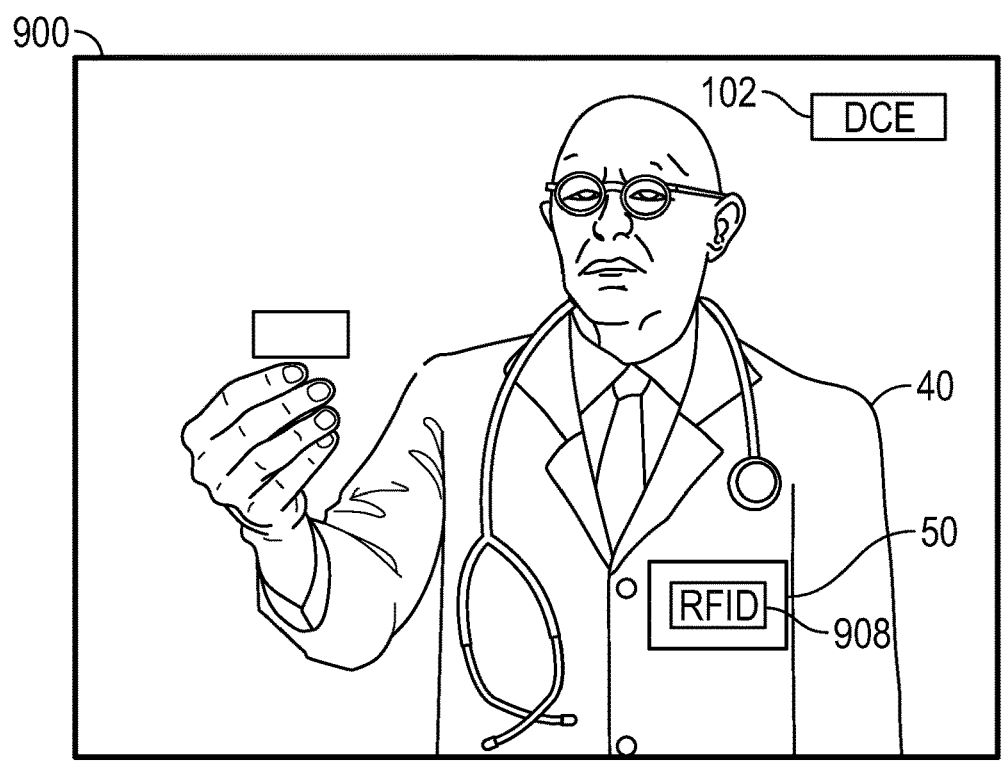
FIG. 9 is an illustration of an exemplary medical professional wearing an identification badge with a RFID tag.

If the RFID chip 910 is a passive type, it can send the data indicative of a first event while receiving power from the DCE 102. In this case, the first event would be the patient 60 being in the medical facility room 900. In FIG. 9, the doctor 40 is wearing a medical professional ID badge 50 including an RFID tag 908. The DCE 102 communicates and receives data from the RFID tag 908 when the doctor 40 enters the medical facility room 900. The RFID tag 908 sends a message including data indicative of a second event to the DCE 102. In this case, the second event is that the patient 60 is being seen by the doctor 40. When the RFID tag 908 in the medical professional ID badge 50 is no longer in proximity to RFID tag 910 in the patient ID badge 70, the RFID tag 910 sends a message including data indicative that the medical appointment has concluded. The RFID tag can include a sensor for detecting near presence of another RFID chip. The DCE 102 can then send one or more messages indicative of the events to be sent to the server device 114 via the network connection. This exemplary embodiment illustrates how the system gathers RFID data such as patient identification, doctor identification, ward location, handover, interval between handovers, etc. as a patient event for data input into the NNM.

Referring to FIG. 6, the operations of the RFID tag and the DCE in a simple scenario will be discussed. At 602 a passive-type RFID chip on an item receives electrical power wirelessly from the DCE. The wireless power can be sent along with a regular general broadcast message from the DCE or an interrogation request. Of course, if the RFID chip is active-type, this step can be omitted. At 604, the RFID tag sends registration information to the DCE, which records it in its memory. Particularly, the registration information can include the identification of the RFID tag. At 606, if the RFID tag and/or the DCE determines that an event has occurred, at 608 the RFID tag sends parameters associated with the event to the DCE. The DCE records the parameters in its own memory or immediately transmits the information to the server to be stored in the medical item database.

Referring to FIG. 7, the operations of the RFID chip and the DCE in a scenario in which a medical professional such as a doctor meets with a patient will be discussed. At 702, the doctor 40 wearing an identification such as a badge including an RFID chip (active or passive-type) 908 enters a room 900 within the communication area of the DCE 102 and the RFID tag 908 registers with the DCE 102. A patient 60 with a patient identification 70 including another RFID tag 910 which has already registered with the DCE 102 is already in the room 900. At 704, the DCE 102 records a first event indicative of the patient 60 and the doctor 40 being in the same room and the start time. At 706, the DCE 102 generates a message representative of this first event to be transmitted to the server. At 708, the doctor 40 wearing the identification 50 including the RFID tag 908 leaves the room 900 and disconnects from the DCE 102. At 710, the DCE 102 records the time the RFID tags disconnected as the end time of the first event and generates a message representative of the end time of the first event to be transmitted to the server.

Figure 12:
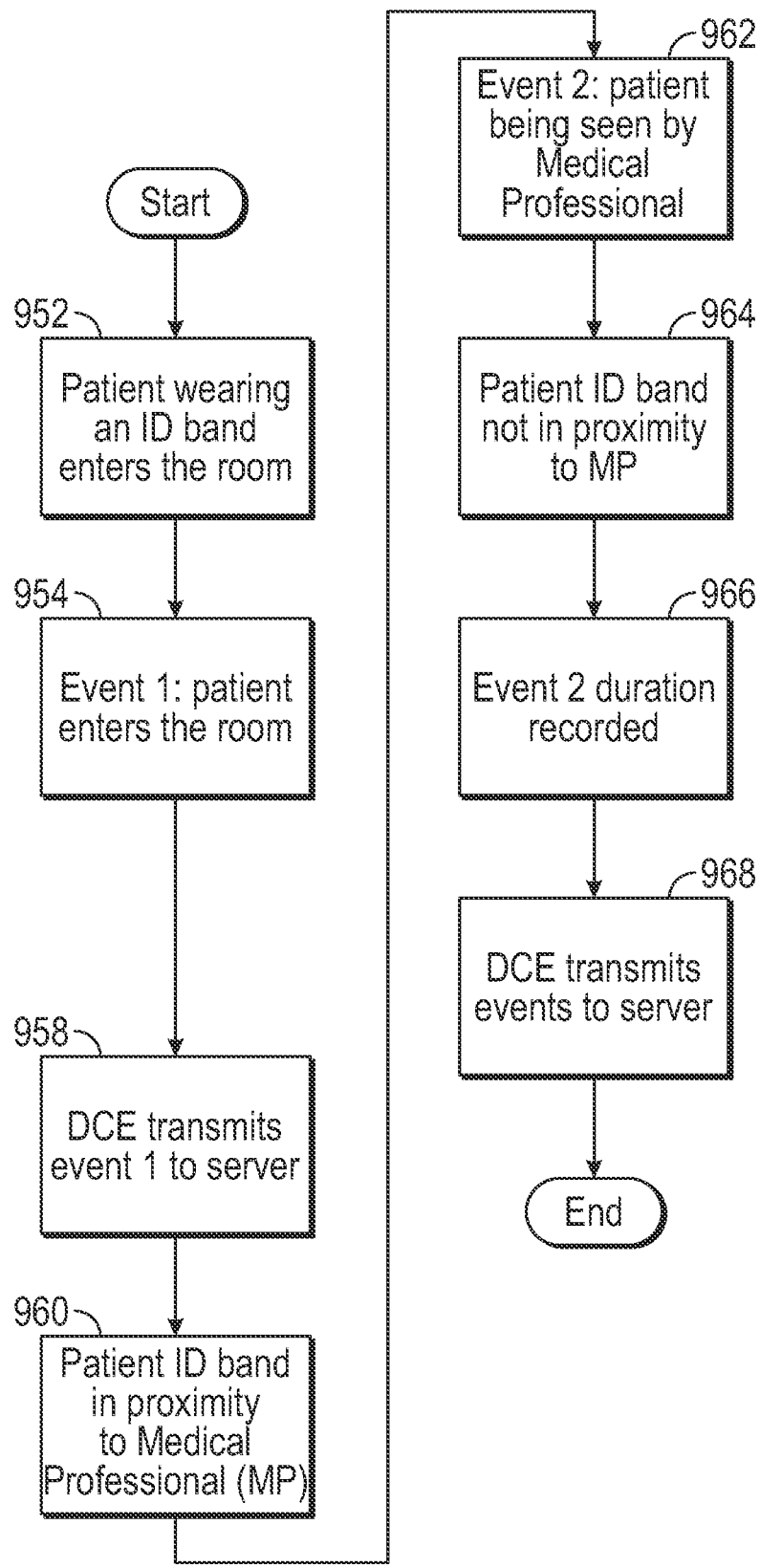
FIG. 12 is a flow diagram illustrating exemplary operations of the system.

Referring to FIG. 12, operations of the system for an exemplary patient event in which a patient arrives to a medical appointment will be discussed. Although the example is different, reference numerals from FIGS. 8-9 will be used again for ease of understanding and brevity. At 952, the patient 60 wearing the patient ID band 70 including the RFID tag 910 enters the room 900. At 954, the DCE 102 establishes communication with the RFID tag 910 and records the location and patient identification as "Event 1". At 958, the DCE 102 transmits a message indicative of "Event 1" to the server. At 960, it is detected that the patient ID band 70 is in proximity to the doctor's ID badge 50. For example, the DCE 102 can receive registration messages from both the RFID tag associated with the doctor's ID badge 50 and the RFID tag 910 of the patient 60 and thereby conclude that the doctor and patient are in the same room.

Alternatively, if one of the RFID tags is an active-type RFID tag while the other is a passive-type RFID tag, if the passive-type is activated by power from the active-type RFID tag, one of these tags can transmit a message to the DCE indicative of this relationship. Further, one of the RFID tags can include a sensor for detecting when another type of RFID tag is within a predetermined distance. At 962, the DCE 102 records a patient event indicative of the patient 60 and doctor 40 being in the same room and the start time. At 964, it is detected that the patient ID band 70 is no longer in proximity to the doctor 40, similar to the detection method of 960. At 966, the DCE 102 records the duration of the patient event as "Event 2". At 968, the DCE 102 transmits the patient event 2 to the server 114. The RFID chips can detect separation from another RFID chip or being within a predetermined distance from another RFID chip by the sensor group. Alternatively, the detection can be performed by ambient radio frequency communication techniques which can detect proximity up to, for example, 70 cm by backscattering. Further, the detection can be performed at the DCE end by, for example, measuring the RSS of the RF signal received from the chips.

Figure 13:
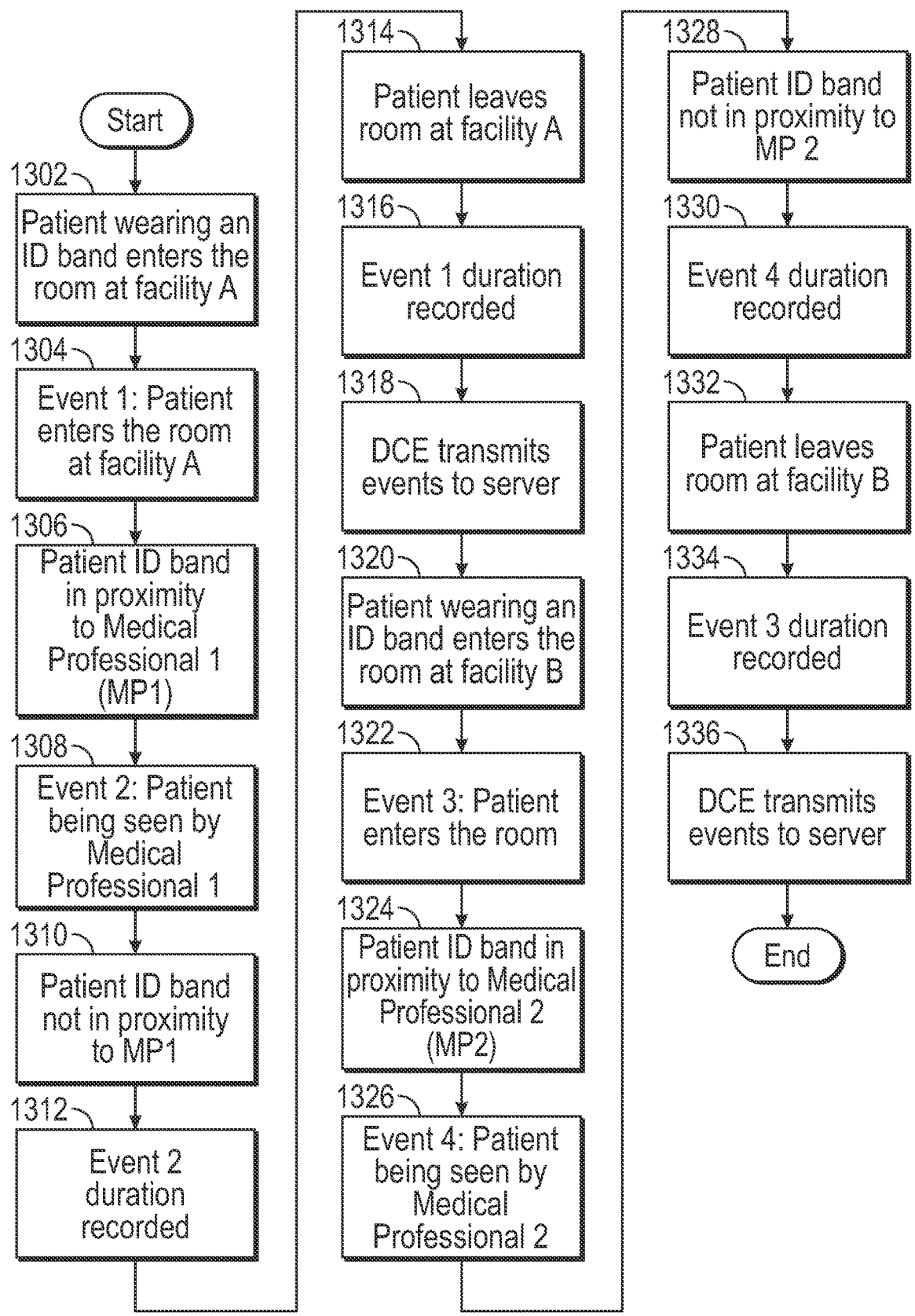
FIG. 13 is a flow diagram illustrating exemplary operations of the system in an example in which a patient is treated at two unaffiliated facilities.

Referring to FIG. 13, operations of the system during an exemplary scenario in which a patient receives care at multiple facilities will be discussed. In this exemplary scenario, the data collected could be whether the patient received medical care from two different doctors at two unaffiliated healthcare providers. At 1302, the patient wearing a patient ID band including an RFID tag enters a room at facility A having a DCE disposed, for example, on the ceiling to define a coverage area. The RFID tag sends a registration message identifying itself to the DCE in response to a polling request or broadcast message. At 1304, the DCE registers the patient associated with the RFID tag in the room as "Event 1". At 1306, the patient becomes in proximity to a medical professional (MP1). It is detected that the RFID tag in the patient ID band detects is in proximity to the RFID chip associated with the first doctor's ID badge by one of the RFID tags, a sensor, and/or the DCE similarly to as discussed with respect to step 960 in FIG. 12. At 1308, the DCE records that the patient is being seen by MP1 based upon the detection as "Event 2". At 1310, the patient ID band is no longer in proximity to the MP1. This can also be detected similarly to as discussed with respect to step 960. At 1312, the DCE records the duration of Event 2 based upon the time from which the RFID tags were in proximity. At 1314, the patient leaves the room at facility A. This can be detected by, for example, the end of communication between the DCE and the RFID tag associated with the patient or based upon location information received from the RFID tag. At 1316, the DCE records the duration of Event 1 based upon when the patient left the room at facility A. At 1318, the DCE transmits the first and second events to the server.

At 1320, the patient wearing the patient ID band including the RFID tag enters a room at facility B having a DCE disposed, for example, on the ceiling to define a coverage area. The RFID tag sends a registration message identifying itself to the DCE in response to a polling request or broadcast message.

At 1322, the DCE registers the patient associated with the RFID tag in the room as "Event 3". At 1324, the patient becomes in proximity to a medical professional (MP2). It is detected that the RFID tag in the patient ID band detects is in proximity to the RFID chip associated with the second doctor's ID badge similarly to as discussed with respect to step 960 in FIG. 12. At 1326, the DCE records that the patient is being seen by MP2 based upon the detection as "Event 4". At 1328, the patient ID band is no longer in proximity to the MP2. This can also be detected similarly to as discussed with respect to step 960. At 1330, the DCE records the duration of Event 4 based upon the time from which the RFID tags were in proximity. At 1332 the patient leaves the room at facility B. This can be detected by, for example, the end of communication between the DCE and the RFID tag associated with the patient or based upon location information received from the RFID tag. At 1334, the DCE records the duration of Event 3 based upon when the patient left the room at facility A. At 1336, the DCE transmits the third and fourth events to the server.

In the above example, the DCE can be separate DCE's at facility A and facility B. Both DCE can register the two events as first and second events, but the server can recognize these as four different events upon receiving the messages indicative of the events from the respective DCE.

The server 114 can recognize the transition between events as a handoff of the patient and store a time interval between handoffs. Returning to FIG. 1, because the server 114 communicates with various input sources besides the RFID tags, the server 114 can use data from these input sources as well as from the RFID tags as an input data set into the trained model to make a prediction as discussed in the second embodiment.

Second Embodiment

Referring to FIGS. 14-36, a second embodiment will be discussed in which the server device 114 utilizes a trained model to make predictions regarding events.

Creating a Trained Neural Network Model to Predict an Outcome

Figure 14:
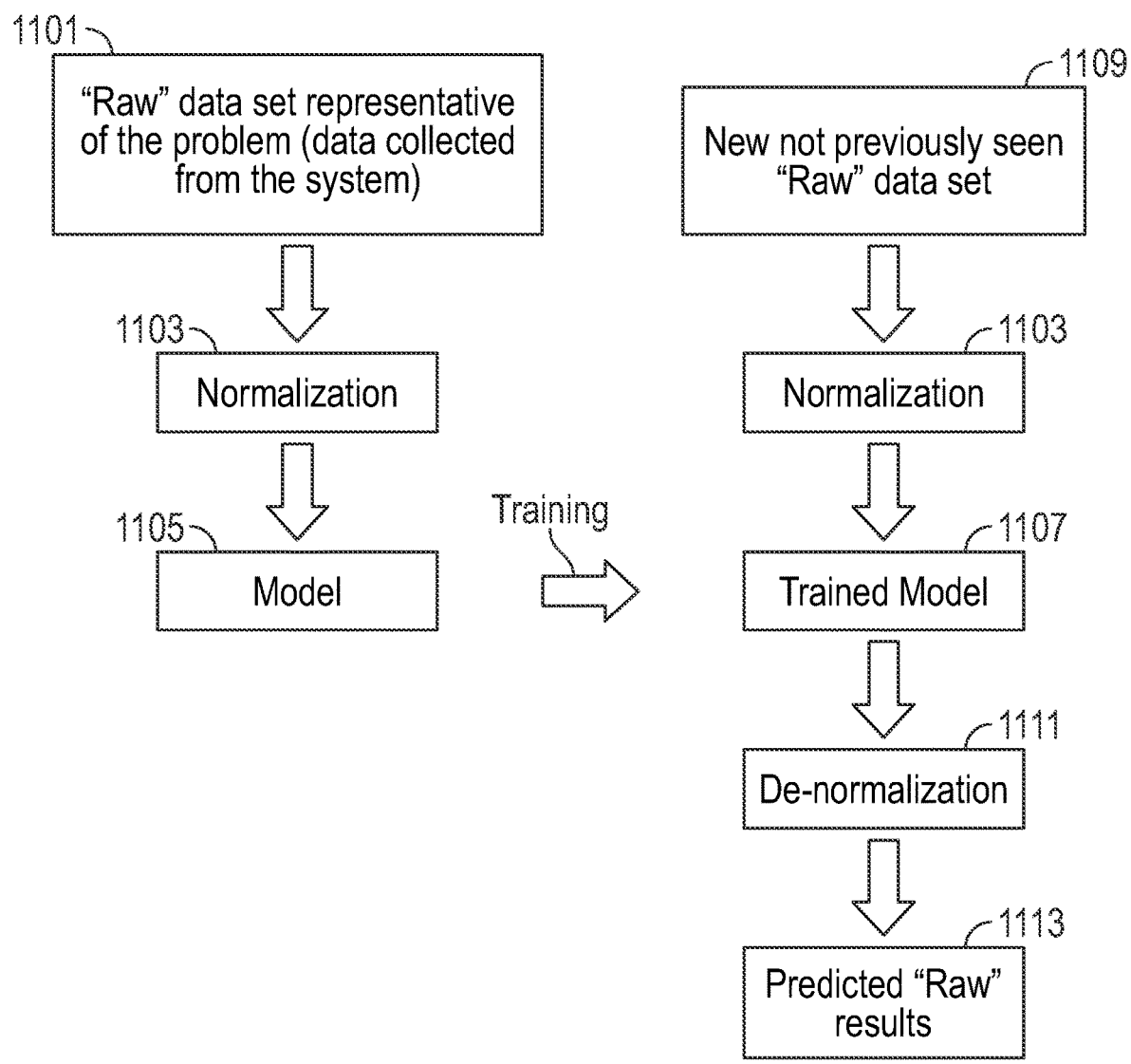
FIG. 14 is a block diagram illustrating high level operations for creating a trained neural network model (NNM) according to an embodiment.

The server device 114 stores a trained model such as, for example, a neural network model which is used to predict an outcome of a clinical patient event. A representation of the process for creating, training and using the trained model is shown in FIG. 14. Raw data 1101 is normalized 1103, and then input into the model 1105. The model 1105 is trained to form the trained model 1107. New data 1109 is normalized 1103 and input into the trained model 1107. The output data of the trained model 1107 is de-normalized 1111 to obtain the output data (predicted raw results) 1113. As shown in FIG. 15, the raw data 1101 and new data 1109 include sets of data [1, 2 ... N] with known outcomes and properties of each of the data. For example, in the case of individual patients, the data can be past patient events with known outcomes (patient had preventable medical error and/or adverse event vs. did not have medical error and/or adverse event, nature/type of preventable medical error/adverse event, hospital location (i.e. ward/room/bed) at time of medical error/adverse event). In the case of hospital locations, the data can be a rate of medical errors and/or adverse events per X number of admissions to a respective location. Below is a non-exhaustive list of example input attribute data.

Input Data Attributes
- Admitting healthcare provider and team members caring for patient (as determined from hospital information systems and/or system's RFID/DCEs)
- Consulting healthcare provider and team members (as determined from hospital information systems and/or system's RFID/DCEs)
- Nurses caring for patient within a given interval of time (as determined from hospital information systems and/or system's RFID/DCEs)
- Handoffs completed by particular personnel (admitting team, consulting team, nurses, other personnel) within a given interval of time
- Patient current and prior locations (i.e. wards, etc.) during a given interval of time as obtained from RFIDs/DCE/hospital information system/HL7 ADT feeds/other
- Handoff training status (date(s) of completion, training completed) of personnel (i.e. admitting team providers, consulting team providers, nurses)
- Provider and/or nurse handoff assessment evaluation scores and dates
- Audio or video data captured from verbal handoff discussions between medical personnel caring for patient
- Content and/or objective quality rating of handoff documentation for patient
- Presence/frequency/dates of handoff documentation
- Handoff workflow data capture (from client device GUI activity, queries and commands) captured during use of client device for carrying out patient handoffs and logged in end user
- Hospital information system data, documentation, and clinical charting The model 1105 is trained by an iterative machine learning algorithm. After initial deployment, the server 114 will also continuously collect data from a variety of sources along with actual related healthcare system clinical and operational outcomes; this data can subsequently be used as training data. As such, the server 114 is able to continuously learn and improve its ability to predict the outcomes of interest. In addition, the knowledge of the system can continue to evolve in the event the system dynamics change.

There is a relationship between the multitude of attribute data the system collects about an event and the outcome in question. However, there is no one specific mathematical relationship or equation that describes the relationship between attributes of the event risk and the outcome of interest. However, because of the server's machine learning capabilities it has the ability to "learn" or be trained from pre-existing data and from the data it collects prospectively. Said another way, the server 114 "learns" from experience.

Data Set Encoding, Normalization and De-Normalization

Neural network models only use numerical double values for training and processing. Thus any nominal categorical data fields that are a part of raw data that will ultimately be used by models in the system are first encoded to numerical values and "raw" numerical data in many cases by a pre-processing such as normalization 1103 before training and processing. While normalization and de-normalization steps may not be explicitly described as being carried out before or after data consumption by any given model, this should not be misconstrued and lead to the assumption that these routine steps are not carried out.

The normalization processes 1103 and corresponding de-normalization processes 1111 are used not only for training data sets, but also for new, unseen data that is fed into the trained models. Though it is not the rule, frequently, the output from the trained models is normalized and in the event it is a categorical data field the output will also be encoded. Thus, often output from the system models has to be de-normalized and possibly decoded to yield the "raw data," "human readable" format of the predicted output.

Neural network training is often more efficient when independent numeric data (x-data) is normalized. For this reason, the system most often normalizes numeric data along the same scale being utilized by the model for all data fields, including nominal data fields. The scale the system utilizes for normalization depends on the particular activation function employed by a given model. In most cases this results in normalization either from −1 to 1 or 0 to 1, however, in some cases intermediate range values may be used as well, such as −0.5 to 0.5, for example. This "raw data" normalization step also prevents predictors or inputs that are relatively larger in magnitude (as compared to other predictors or inputs) from having more relative influence on the change in the value of synaptic weights during training of the system models. For problems with normalized nominal data, one neuron is required to represent each numeric data field type.

Figure 16:
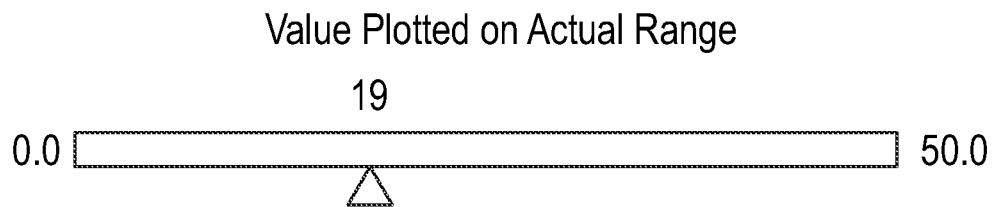
FIGS. 16-17 are illustrations of various exemplary approaches for normalizing the data set.

An example of one of the independent predictors (input x-data) or discharge attributes that can be utilized by the system is the number of medications a given patient is prescribed at the time of discharge. Suppose a patient has 19 discharge medications and that this "raw data" value needs to be normalized to a −1 to 1 normalization range. If the actual range of the possible number of discharge medications is 0 to 50, for example, then to normalize this input x-data, the system's continuous or numeric normalization process would carry out normalization calculations similar to those illustrated herein. Initially, the value can be plotted on an actual range as shown in FIG. 16. Then a normalization calculation can be carried out as shown below:

{[(19−0.0)*(1.0−(−1.0))]/(50.0−0.0)}+(−1.0)=−0.24

Figure 17:
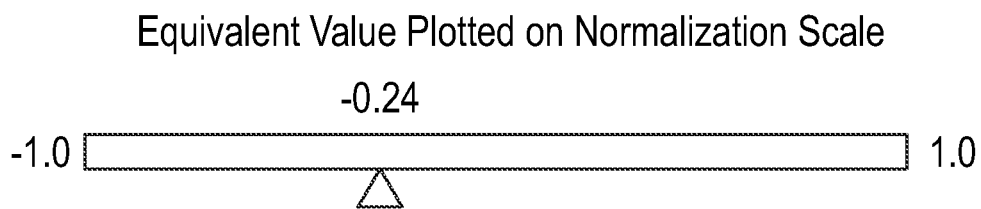
Figure 18:
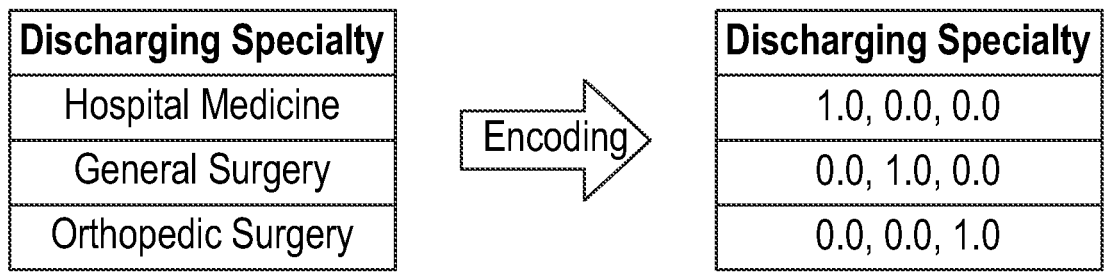
FIG. 18-19 are illustrations of various exemplary approaches for encoding the normalized data set.

Referring to FIG. 17, equivalent value plotted on a normalization scale is shown. In the encoding process, the system may encode classification labels into double values within the normalization range such as −1 to 1 or 0 to 1. The scale the system utilizes for encoding depends on the particular activation function employed by a given model. An approach the system employs at times to encode nominal data fields is so called one-of-N encoding as shown in FIG. 18. For example, one of the attributes that may be used is the medical specialty. In this case, the attributes have three medical specialties: hospital medicine, psychiatric care and community organizations. The nominal categories are represented by double values within a normalization range of 0 to 1. Another variety of this approach that can be used is one-of-C-dummy encoding. When this method is employed, the number of neurons needed to represent a given number of nominal data field types is equal to the number of distinct nominal categories. However, one-of-N encoding is subject to an unequal distribution of error (unequal fault behavior) for wrong predictions which can occur when there are more than two nominal categories. For example, if the value predicted by a given model is psychiatric care {0.0, 0.0, 1.0} but the ideal (real) value is actually psychiatric care {0.0, 1.0, 0.0} as shown, it is apparent that there is only error in two parts. Said another way, if the predicted and the ideal (real) values are compared, the first value is 0.0 in both (i.e. is correct), while the other two values are both wrong. This is unequal distribution of errors.

Figure 19:
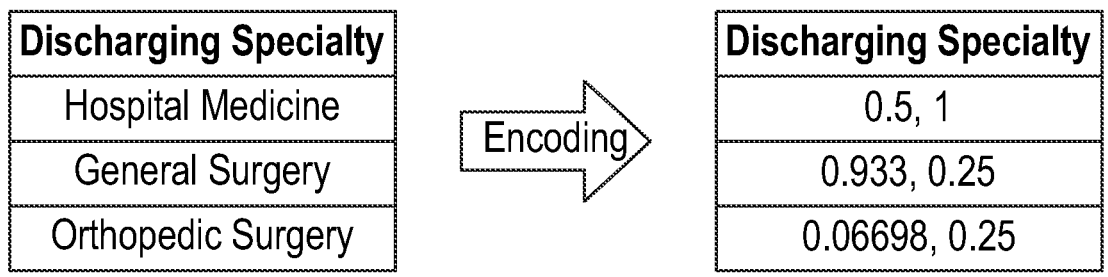

Due to this shortcoming of one-of-N encoding, particularly in instances when there are more than two nominal categories, the server can employ equilateral encoding (one-of-(N-1) encoding shown in FIG. 19 or one-of-(C-1) dummy encoding for encoding nominal categorical data. When equilateral encoding is used fault behavior is equally distributed when wrong predictions are encountered. The equilateral encoding used by the system is based on the Euclidean normalization technique which results in each nominal category having equal Euclidean distances from the others. The Euclidean Distance is calculated as shown below:

$$distance = \sqrt{\frac{(i_1 - a_1)^2 + (i_2 - a_2)^2 + \ldots + (i_n - a_n)^2}{n}}$$

Where the variables represent the following:
i=ideal (real) output value
a=actual (predicted) output value
n=number of sets of ideal and actual values With equilateral encoding, all classes are able to be represented by a number of doubles equal to one minus the total number of nominal data classes, in this case 2 (3−1=2). When this technique is used, every set of possible ideal and actual combinations in the above example will result in an equivalent Euclidean distance.

Ideal: {0.5, 1} Actual: {0.933, 0.25}
Euclidean Distance:
=((0.5−0.933)²+(1.0−0.25)²)^(1/2)
=(−0.4332+0.752)^(1/2)
=(0.187489+0.5625)^(1/2)
=(0.749989)^(1/2)
=0.8660
Ideal: {0.06698, 0.25}
Actual: {0.5, 1}
Euclidean Distance:
=((0.06698−0.5)²+(0.25−1)²)^(1/2)
=(−0.433022+(−0.752)^(1/2)
=(0.1875063204+0.5625)^(1/2)
=(0.7500063204)^(1/2)
=0.8660

Equilateral encoding is not employed by the system in scenarios where there are less than three distinct nominal categories.

Exemplary embodiments of a supervised and unsupervised neural network training algorithm used to create a trained model will be discussed. However, these embodiments are merely examples. Those skilled in the art know a variety of machine learning algorithm approaches can be used for the purpose of training system models including, but not limited to support vector machines, genetic programming, Bayesian statistics, decision trees, case based reasoning, information fuzzy networks, clustering, hidden Markov models, particle swarm optimization, simulated annealing, among others.

There are three primary categories of machine learning tasks: classification, regression and clustering tasks.

Classification

Figure 20A:
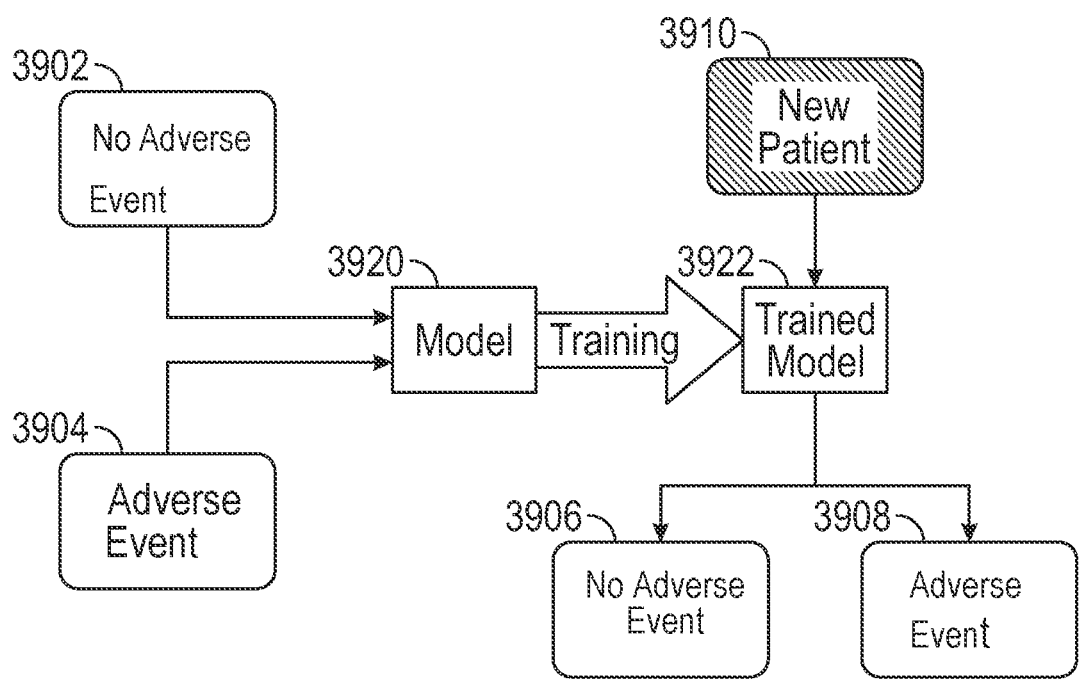
FIGS. 20A-20B are illustrations of a case in which the model is used to categorize the adverse event risk of a plurality of patient events.
Figure 20B:
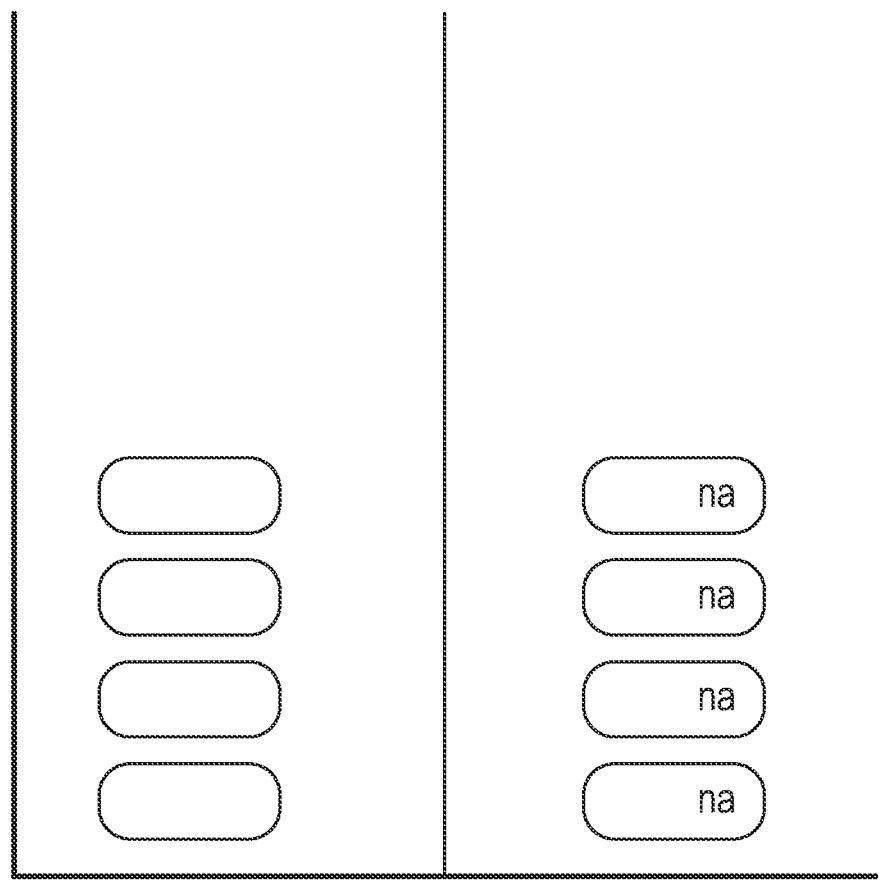

Referring to FIG. 20A-20B, a classification task for predicting an event risk is shown. The machine learning task entails a two-step supervised learning process which utilizes both input and output data in the model training process. Model construction is done using a representative training data set and the model 3920, once trained 3922 is used for classifying new or unseen cases. The inputs are collected risk data attributes/properties such as no patient adverse event 3902 and patient adverse event 3904 or no facility adverse event and facility adverse event. The output for a new patient 3910 will be the predicted categorical risk for an adverse event 3908 or no adverse event 3906 as one example or a facility adverse event or no facility adverse event as another example.

Regression

Referring to FIG. 21, a regression task entails a two-step supervised learning process which utilizes both input and output data in the model training process. Model construction is done using a representative training data set and the model once trained, is used to predict the output (numerical or continuous data) for new or unseen cases. The output can be, for example the anticipated length or duration of discharge delay (a quantity of time).

Clustering

Clustering tasks carried out in the server entail an unsupervised learning process. For clustering tasks, categories and outcomes are not known, or if known are not used for model training. Models are trained from the inputs of the data set, again without or ignoring the corresponding outputs, and from these the model training algorithm tries to identify similarities among the input data and cluster the data based on these learnings, so called "unsupervised learning." The backend devices employ each of these categories of machine learning tasks.

Unsupervised Learning

The server 114 in some instances utilizes unsupervised learning techniques (for example Self-Organizing Map (SOM)—also known as Kohenen Map, Singular Value Decomposition (SVD), and Principal Component Analysis (PCA)) for the purpose of dimensionality reduction. This is done to reduce the input data sets from a large number of dimensions to a lower number of dimensions, such as, for example, to two or three dimensions. This is often employed as a pre-processing step in advance of the application of supervised learning methods. By leveraging unsupervised learning for the purpose of dimensionality reduction, the system is able to reduce the processing (training) time and improve model accuracy. Some supervised machine learning techniques work very well on data sets with a low number of dimensions, however, when there are a very large number of dimensions, performance can degrade, the so called "curse of dimensionality." Thus, the employment of dimensionality reduction techniques actually boosts model performance and efficiency for some tasks.

Another exemplary task, for which the server 114 uses unsupervised learning, as detailed further later herein, is data visualization. Humans are quite facile with the visualization of data in two or three-dimensional space, however visualizing data with more than three dimensions is not a task for which humans are well suited. One of the ways the system overcomes this is by using its unsupervised learning dimensionality reduction capabilities to make patterns in n-dimensional data more easily perceptible to human end users. Thus, the server's dimensionality reduction techniques significantly boost its ability to make data actionable by making the visibility of meaningful, yet complex patterns, more perceptible to its human end users.

Supervised Learning

The backend devices can use supervised machine learning techniques.

Figure 22:
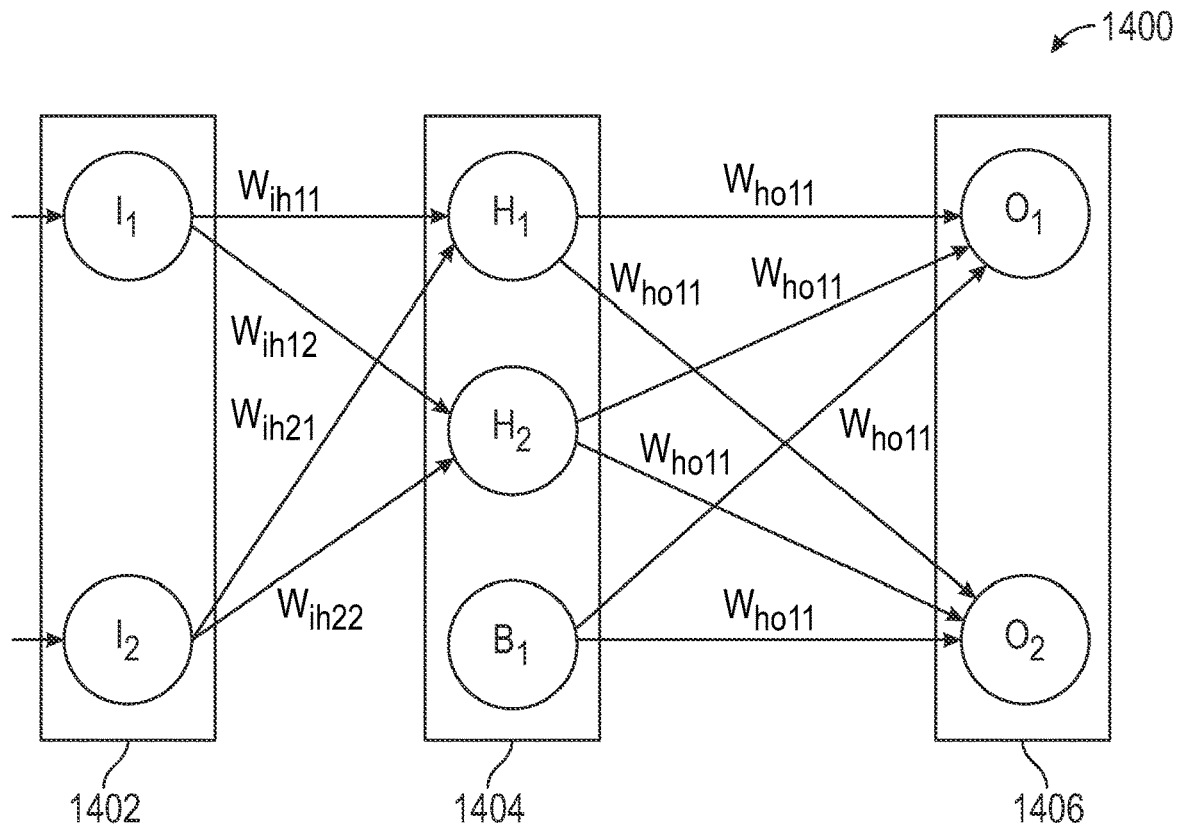
FIG. 22 is an illustration of an exemplary simple feed forward NNM.

Referring to FIG. 22, the backend devices can use a neural network model (NNM) 1400. The NNM 1400 includes an input layer 1402, a hidden layer 1404 and an output layer 1406. The input layer 1402 includes input neurons ($I_1$ and $I_2$) which provide input signals to the network without any processing units (processing units, described further herein are comprised of summation and activation functions). The hidden layer 1404 includes hidden neurons ($H_1$ and $H_2$) which provide a means to converge the network's solution leveraging additional processing units (summation and activation functions). At times, if these neurons are not present, the neural network may not be able to output the desired result. The hidden layer 1404 can also include bias neurons ($B_1$) to provide bias values if there is a requirement for non-zero results. Essentially, they provide a way to obtain a non-zero result even if the input is zero. These most typically do not have any incoming connections, but rather instead, their input values are fixed, for example being fixed with a value of one (1). The output layer 1406 includes output neurons ($O_1$ and $O_2$) containing processing units (summation and activation functions) which provide the means for obtaining the final output of the neural network. A typical neural network employed by the system is comprised of one input layer, one output layer and a plurality of hidden layers (zero or more). The number of neurons the system employs in its neural network input and output layers varies.

In the neural network, connections between neurons have a connection weight or synaptic weight, for example the connection between $I_1$ and $H_2$ has a synaptic weight of $W_{ih\ 12}$. The $W_{ih\ 12}$ notation means the synaptic weight of the connection from input neuron $I_1$ and hidden neuron $H_2$. This synaptic weight denotes the strength of the connection, the higher the weight the higher the strength and vice versa. This synaptic weight determines the effect the synapse has on processing. The synaptic weight is also directional. Said another way, this means the connection from $I_1$ to $H_2$ is different from that from $H_2$ to $I_1$. Thus the notation $W_{ih\ 12}$ not only denotes the neurons that are connected or involved but also the direction of the connection.

Figure 23:
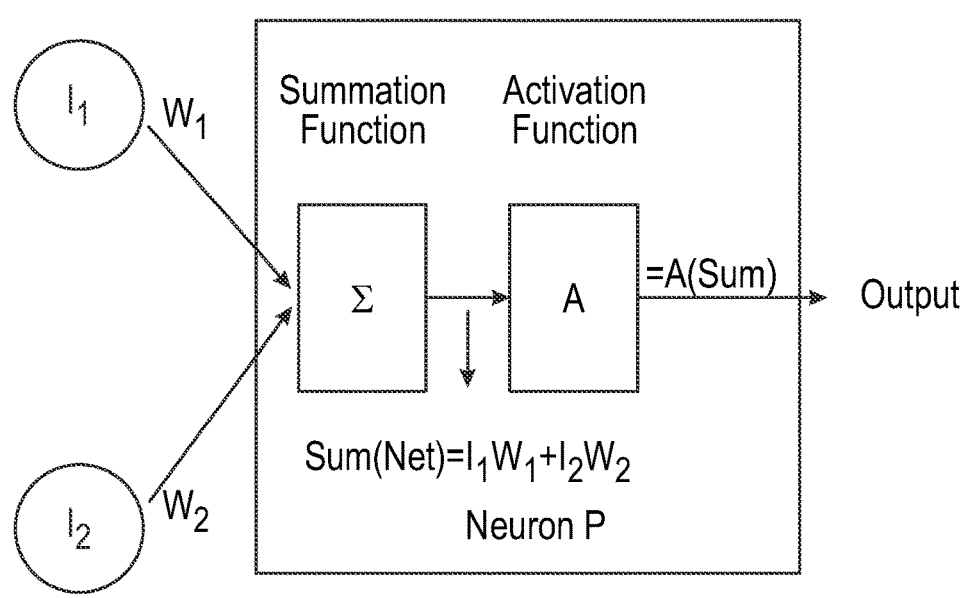
FIG. 23 is an illustration of an exemplary neuron of the NNM.

As shown in FIG. 23, a neural network neuron includes the summation function and activation function. The summation function sums input signals based on their signal strength, or weights. The sum value is also known as Net. The output of the summation function is the weighted sum of input signals. The activation function of a neuron takes the weighted sum of the input signals and performs some calculations to arrive at the output value. Some examples of activation functions used by the system include:

The Sigmoid Function $$f(x) = \frac{1}{1+e^{-x}}$$

Figure 24A:
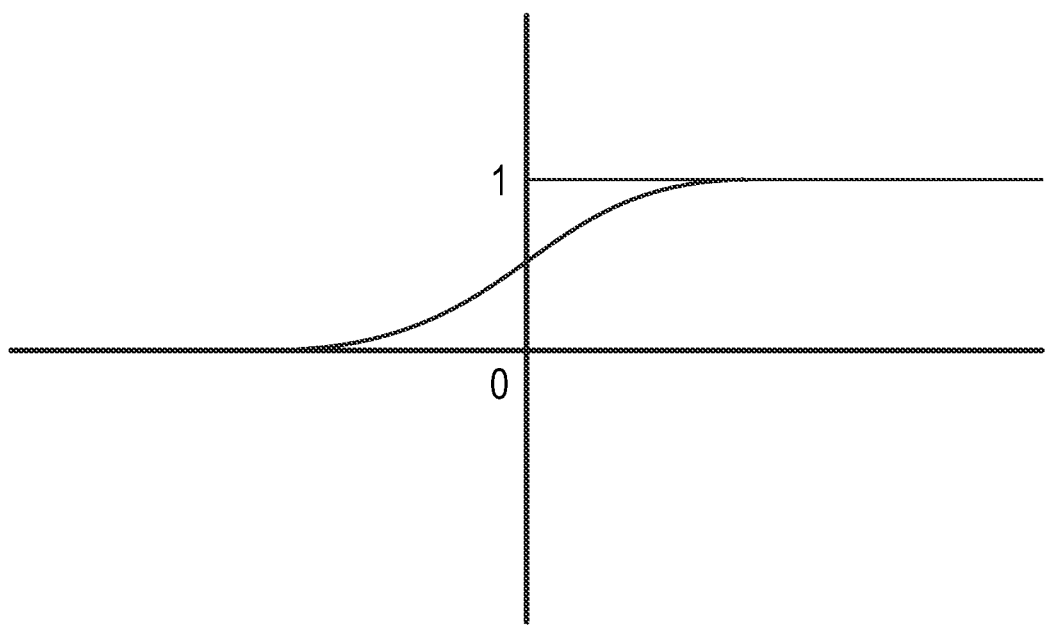
FIGS. 24A-24C are illustrations of exemplary activation functions for the neurons of the NNM.

As shown in FIG. 24A, a characteristic of the sigmoid function is that for all values on the x axis, the function output value (y axis) will lie between 0 and 1. The sigmoid function is used in instances where only positive outputs are expected.

The Hyperbolic Tangent Function $$f(x) = \frac{e^{2x}-1}{e^{2x}+1}$$

Figure 24B:
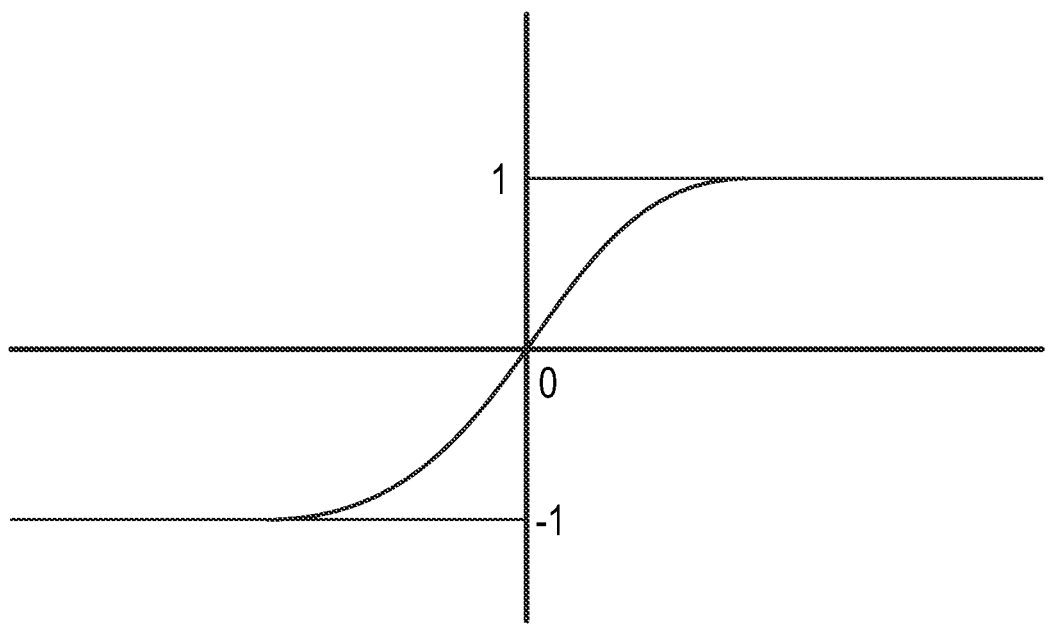

As shown in FIG. 24B, a characteristic of the hyperbolic tangent function is that for all values on the x axis, the function output (y axis) will lie between −1 and 1. The hyperbolic tangent function is used by the system in instances when both positive and negative outputs are expected.

The Linear Function $$f(x)=x$$

Figure 24C:
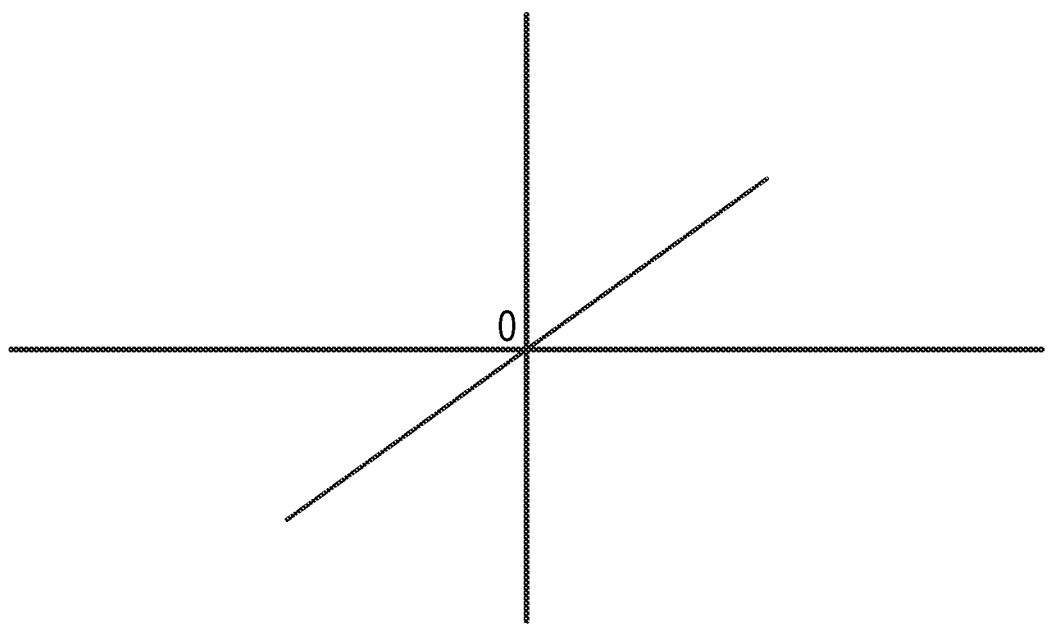

As shown in FIG. 24C, a characteristic of the linear function is that the input and output are the same. The linear function is used by the system in instances where the objective is to replicate the input signal to the output.

The activation functions detailed above are exemplary of activation functions used by the inventive system. One skilled in the art will understand that there are also other activation functions that can be used in neural networks. This disclosure is not intended to be exhaustive, but is intended to describe the fact that the server 114 employs a plurality of activation functions to accomplish its objectives.

Figure 25:
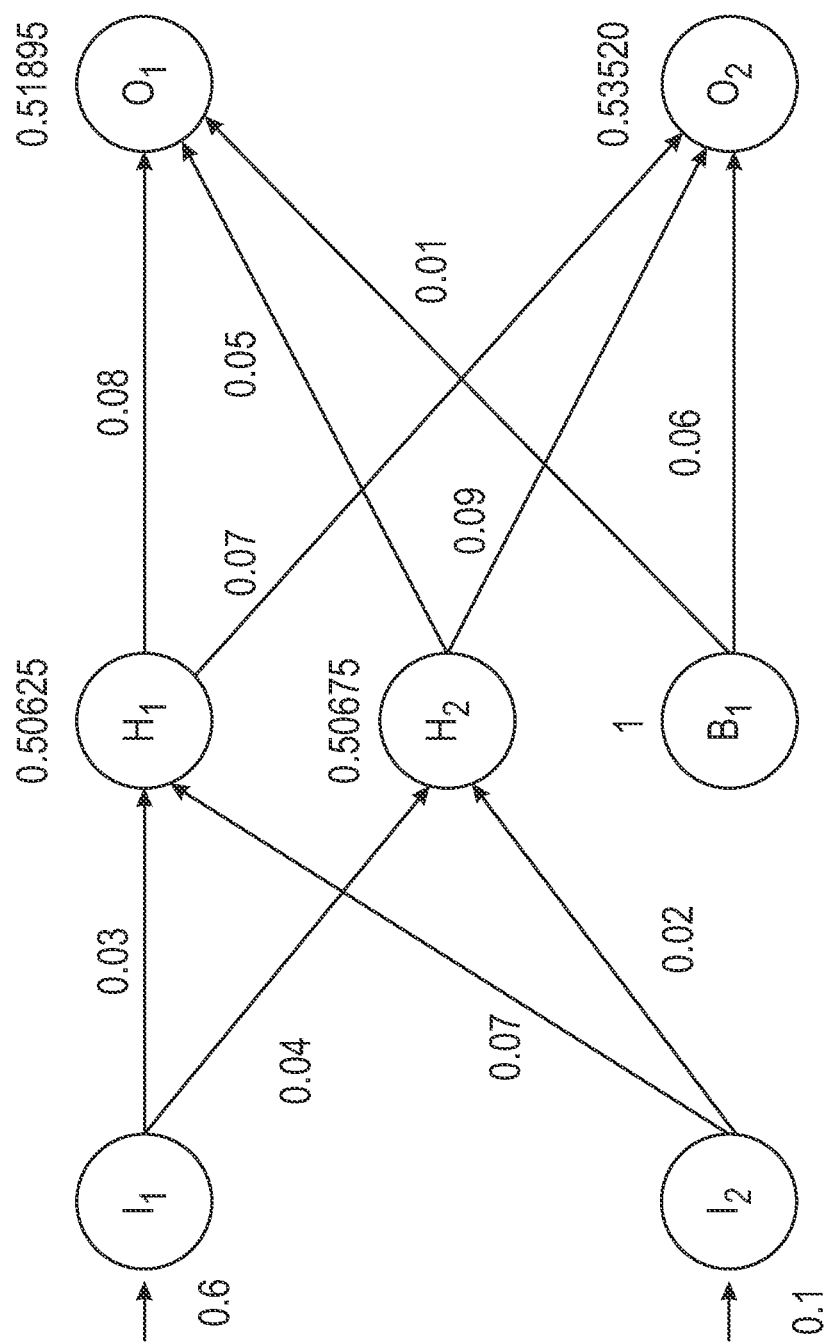
FIG. 25 is an illustration of exemplary computations of the NNM.

A NNM is a neural network architecture with a particular structure tailored to a particular problem statement. An exemplary problem statement for the server's Neural Network Model is the prediction of risk of medical error and/or adverse event and predicted rate of medical errors and/or adverse events per X admissions (or per X admissions with Y primary diagnosis) for a given hospital ward. Using a trained NNM, the server 114 predicts the likely outcome using a plurality of the properties or attributes of the patient event (the inputs). Each model in the system contains input, output, bias and hidden neurons. The input and output neurons are required whereas the bias and hidden neurons are optional depending on the nature of the specific problem statement and its requirements. Each model also has a structure. The exemplary neural network herein depicted in FIG. 25 is demonstrative of a feed forward structure, however other possible neural network structures or architectures include, but are not limited to ADALINE Neural Network, Adaptive Resonance Theory 1 (ART1), Bidirectional Associative Memory (BAM), Boltzmann Machine, Counter propagation Neural Network (CPN), Elman Recurrent Neural Network, Hopfield Neural Network, Jordan Recurrent Neural Network, Neuroevolution of Augmenting Topologies (NEAT), Radial Basis Function Network, Recurrent Self Organizing Map (RSOM), Self Organizing Map (Kohonen), among others. Feedback networks, for example Elman and Jordan Networks, are at times leveraged by the system particularly in instances where the sequence of events (order of data) is material. Each neural network model also has a defined activation function. In the exemplary neural network of FIG. 25, the activation function is the sigmoid function. Prior to model training, the model's neurons and their structure as well as the activation function are defined. The training of a model starts with the random selection of a set of initial synaptic weights. During the training process, the synaptic weights are updated after each training iteration (see further description provided herein). The calculation process below describes how the values at the neural network nodes $H_1$, $H_2$, $O_1$ and $O_2$ are calculated for given inputs $I_1$ and $I_2$ and a given set of synaptic weights (synaptic weight values for this example are those shown in FIG. 25). This calculation process is used during each model training iteration and subsequently when the trained model is used to make predictions from previously unseen input data:

$H_1$ $\text{Sum} = 0.6*0.03 + 0.1*0.07$ $= 0.018 + 0.007$ $= 0.025$ $\text{Output} = A(\text{Sum}) = 0.50625$ $H_2$ $\text{Sum} = 0.6*0.04 + 0.1*0.02$ $= 0.024 + 0.002$ $= 0.027$ $\text{Output} = A(\text{Sum}) = 0.50675$ $O_1$ $\text{Sum} = 0.50625*0.08 + 0.50675*0.05 + 1*0.01$ $= 0.0405 + 0.0253375 + 0.01$ $= 0.0758375$ $\text{Output} = A(\text{Sum}) = 0.51895$ $O_2$ $\text{Sum} = 0.50625*0.07 + 0.50675*0.09 + 1*0.06$ $= 0.0354375 + 0.0456075 + 0.06$ $= 0.141045$ $\text{Output} = A(\text{Sum}) = 0.53520$ During the training process, the synaptic weights are adjusted to minimize the error of the output. Thus, the final synaptic weights of the trained model are only known once model training is complete. After successful training of the model, the finalized synaptic weights are then used to make predictions.

Training the NNM

To train the NNM, the controller iteratively performs a machine learning algorithm (MLA) to adjust the values of the synaptic weights until a global error of an output of the NNM is below a predetermined acceptable global error. Performing of the MLA includes: generating an output value of the NNM for each past patient event in the training data set using each patient event's respective input data attributes; measuring the global error of the NNM based upon the output values of the NNM and the quantifiable outcomes of the past patient events; and adjusting the values of the synaptic weights if the measured global error is not less than the predetermined acceptable global error to thereby obtain a trained NNM. Here, if the global error is never reached after number of outcomes, the model can be revised, such as number of hidden layers, neurons, etc.

There are two types of error that pertain to neural networks. The first is Local Error (E). Local error is the actual output value computed by the neural network subtracted from the ideal value (i.e. the output value in the training data set). This error is "localized" to particular output neurons, hence the name local error. The other type of error is the error of the neural network, also called network error or global error. The global error is the cumulative effect of the error at each of the outputs (the local error for each output). There are a few types of global error which are briefly discussed below.

Mean Square Error (MSE)

$$\frac{\sum_n E^2}{n}$$

The mean square error (MSE) is the sum of the square of all local errors divided by the total number of cases.

Sum of Square Errors (ESS)

$$\frac{\sum_n E^2}{2}$$

The sum of square errors (ESS) is the sum of the square of all local errors divided by two (2).

Root Mean Square Error (RMS)

$$\sqrt{\frac{\sum_n E^2}{n}}$$

The root mean square error (RMS) is the square root of the MSE.

The system generally uses MSE, however, in some specific instances the other methods for determining the global error are used.

To more formally state the objective of using machine learning to train the models in the system, it is most accurate to say that the system employs machine learning algorithms and training data to adjust the synaptic weights for the connections in each model such that the global error is less than a pre-established level. The system is configured with acceptable global error levels that balance the tradeoffs of model overtraining (acceptable global error level too low) and model undertraining (acceptable global error level too high).

Figure 26:
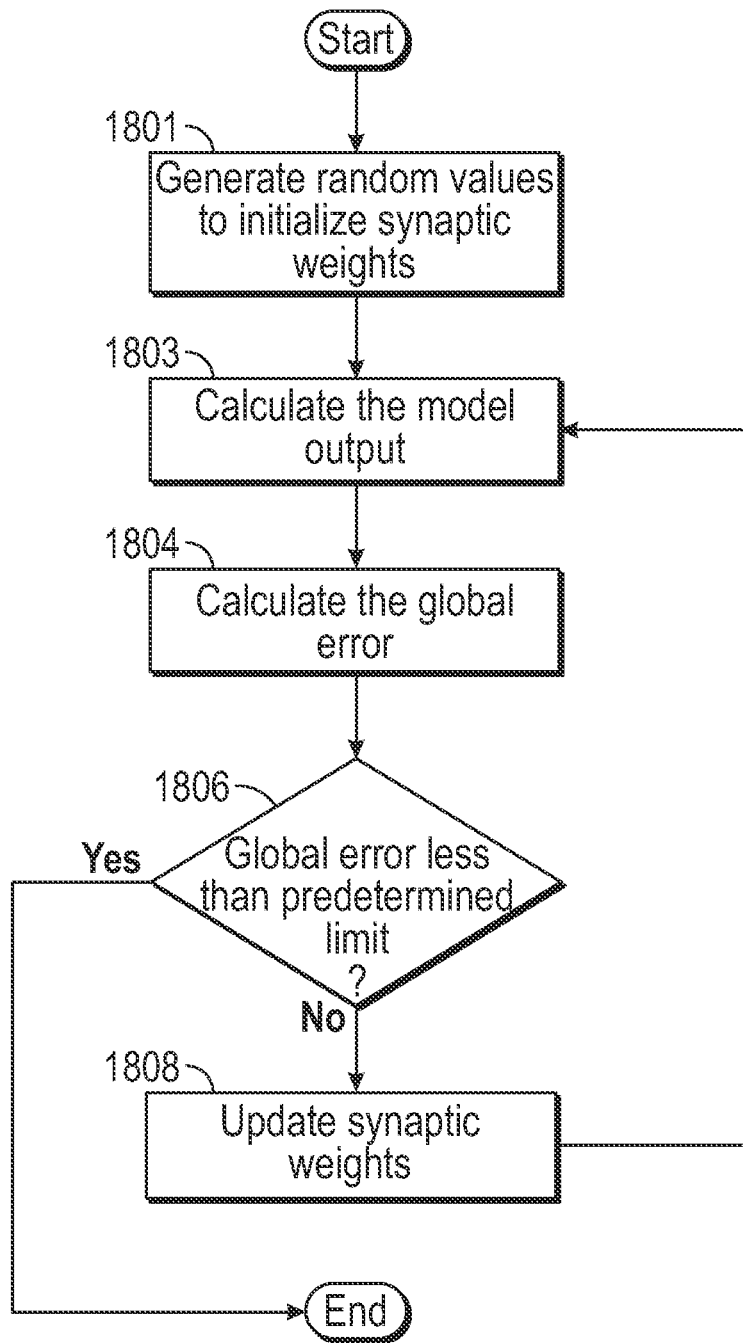
FIG. 26 is a flow diagram illustrating exemplary operations of the system for training the NNM.

Referring to FIG. 26, the approach for training the NNM based upon training data will be discussed. The training data is quantifiable outcomes (rate of medical errors per X admissions to hospital ward A, or the rate of medical errors per X admissions to hospital ward A with a primary diagnosis of Y suicide attempt or no suicide attempt) of a plurality of past patient events and patient attributes of each of the past patient events. Initially, at 1801, values of the plurality of synaptic weights are assigned to random values. At 1803, the output values of the model are calculated for the current "row" or case in the training data being used for the current training iteration (i.e. "row" being the one event or case used for the current training iteration out of the available events in the training data set) using the initial random synaptic weights. At 1804, the global error for this iteration of the NNM training process is calculated. Particularly, a local error at each of the output(s) is calculated, which is the difference between each output value of the NNM on this iteration and the corresponding actual (known) quantifiable outcomes from the current "row" in the training data set. The global error is then calculated by summing all of the local errors in accordance with MSE, ESS and/or RMS discussed above. If it is determined that the global error is not less than a predetermined acceptable global error (NO at 1806), the values of the synaptic weights are adjusted at 1808, and a new training iteration using another patient event from the training data set begins (at 1803). As part of this next iteration, the global error is again calculated at 1804. Here, if the global error is never reached after a number of iterations, the model can be revised, such as changing the number of hidden layers, neurons, etc., and the training process can be attempted again. When it is determined that the global error is less than the predetermined acceptable global error (YES at 1806), the trained model is then subjected to validation discussed later.

Different machine learning algorithms as well as different global error calculation methods can be employed to update the synaptic weights. Some of the machine learning algorithms the server can be configured to employ include ADALINE training, backpropagation algorithm, competitive learning, genetic algorithm training, Hopfield learning, Instar and Outstar training, the Levenberg-Marquardt algorithm (LMA), Manhattan Update Rule Propagation, Nelder Mead Training, Particle Swarm (PSO) training, quick propagation algorithm, resilient propagation (RPROP) algorithm, scaled conjugate gradient (SCG), among others. Machine learning algorithm selection is determined based on a number of factors some of which include accuracy of the algorithm, the computation resources available and those required of the algorithm, the available or ideal training time duration, among others.

Figure 27:
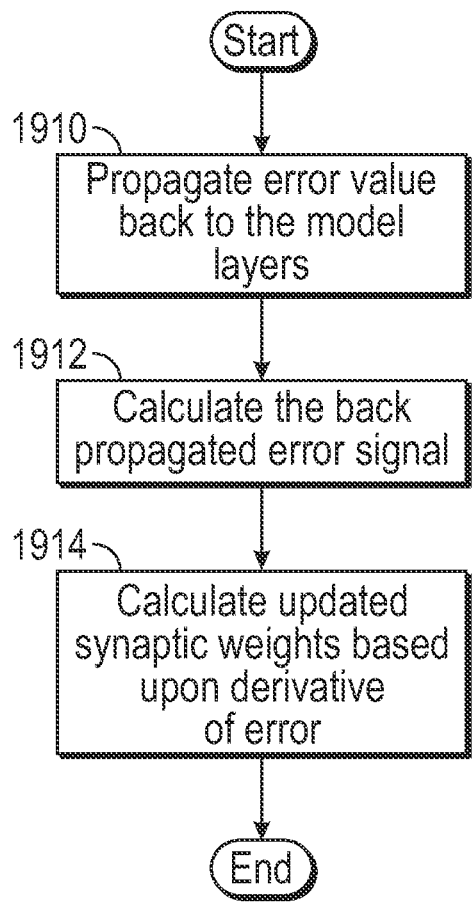
FIG. 27 is a flow diagram illustrating exemplary operations of the system for propagation training (updating the synaptic weights between iterations) of the NNM.

Training the system models is an iterative process referred to as propagation. As discussed above, the process begins by using randomly assigned synaptic connection weights to compute the outcome of the model (1803). Using the known output values for cases in the training data set and the output values computed by the model, the local error at each output, and subsequently the global error of the network is determined (1804). If the global error is not below the pre-established acceptable global error rate a new iteration with updated synaptic weights will ensue. The process for updating the synaptic weights (1808) is referred to as propagation training. As already discussed, the system can be configured to employ one of a variety of methods (algorithms) for updating the synaptic weights during the training process for a given model. Referring to FIG. 27, a gradient-decent procedure can be used to update the synaptic weights on each training iteration. At 1910, the error value is propagated to the model layers. The gradient-decent procedure is used to determine the direction of change of the synaptic weight (s) that will minimize error on the next iteration. Doing this requires model neurons to use differentiable activation functions, such as those already previously discussed herein. At 1912, the back propagated error signal is determined by calculating the error gradient (gradient-decent procedure). The error gradient is the value of the instantaneous slope at the current point on the error function surface plot. Said another way, the error gradient is the derivative value of the error function surface plot, the plot of the error values that correspond to different synaptic weights. The proportion of the error gradient that is used in each iteration of the propagation process is called the learning rate and can be configured in the system (essentially, how much of the derivative value should be applied to update the synaptic weights on each model training iteration). This procedure can vary depending on the propagation algorithm employed by a given model in the system. The larger the learning rate, the larger the synaptic weight changes will be on each iteration and the faster the model will learn. However, if the learning rate is too large, then the changes in the synaptic weights will no longer approximate a gradient decent procedure (a true gradient decent is predicated on infinitesimal steps) and oscillation of the synaptic weights can result (no learning at all). Conversely if the learning rate is too slow, training of the model will be a very lengthy process utilizing large amounts of compute time. The learning rate that is used for training the system models is one that results in brisk learning without triggering oscillation. When the system is configured with optimal learning rates the fastest training of each model is achieved with the smallest compute training time expenditure.

The model propagation training process utilized by the system can also employ the concept of momentum to deal with the challenge of local minima that can complicate backpropagation (the process of following the contour of the error surface with synaptic weight updates moving in the direction of steepest decent), for example, when the network architecture includes a hidden layer. Momentum is the concept that previous changes in the weights should influence the current direction of movement in the weight space (essentially the percentage of previous iteration weight change to be applied to the current iteration). As such, the inclusion of the momentum parameter can help networks employed by the inventive system to "roll past" local minima. In addition, the inclusion of the momentum parameter can also help speed learning, particularly when long flat error surfaces are encountered. At 1914, the updated synaptic weights are calculated based upon the derivative of the error, the defined learning rate and the momentum parameter.

Training and Validation of System Models

To validate the NNM, the controller generates an output value of the trained NNM for each past patient admission and hospital ward admission events of the validation data, wherein each of the output values represents a calculated quantifiable outcome of the respective patient risk for medical error during the admission or, in the case of the hospital ward analysis, the predicted rate of medical errors per X admissions to the respective hospital wards in the validation data set; the controller then determines if the output values correspond to the known quantifiable outcome within the predetermined global error. The creation and training of the NNM can be repeated until validation data results are satisfactory, defined as output data from the NNM being within the acceptable level of global error from the output values in the validation data set.

Figure 28:
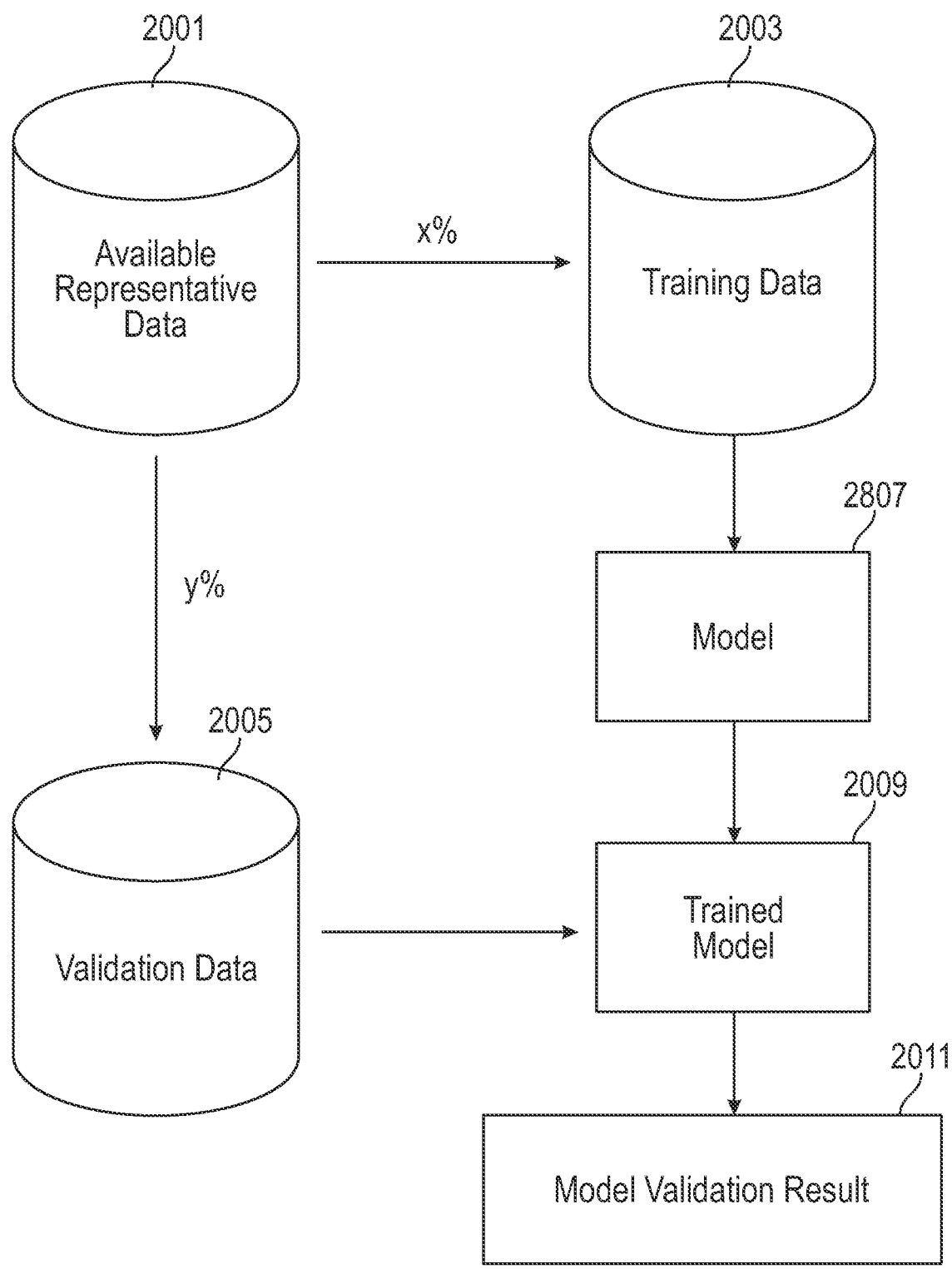
FIG. 28 is block diagram illustrating high level operations of the process for training the NNM and validating the trained NNM.

The training process for the NNM employs a representative data set, which can be a plurality of past patient events as discussed above. Referring to FIG. 28, the cases in the representative data set 2001 are divided into two unique data sets by some ratio or percent x allocated to the training data set 2003 and percent y allocated to the validation data set 2005. The ratio of cases allocated to the training data set 2003 versus those allocated to the validation data set 2005 varies. Before the allocation of cases to the training data set 2003 or the validation data set 2005, an optional step of data shuffling can be carried out by the system to help ensure all types of data in the representative data set 2001 gets distributed to both the training 2003 and the validation 2005 data sets. The training data set 2003 was used to train the NNM 2009 as discussed above. The validation data set 2005 can be used to validate the trained NNM 2009 because the real outcome of each case in the validation data set is known. The server can generate an output value (model validation result) 2011 of the trained NNM 2009 for each past patient event of the validation data set 2005, wherein each of the output values 2011 represents a calculated quantifiable outcome of the respective patient event. Then the server can determine if the output values 2011 correspond to the quantifiable outcome within the predetermined global error.

The training data set 2003 along with the defined system models 2807, the selected machine learning training algorithms and the method each uses for global error calculations, in conjunction with the pre-defined acceptable global error rates are used to train the NNM starting with randomly assigned synaptic weights for each model's neuronal connections. The requisite number of synaptic weight calculation iterations are executed until an acceptable global error level is obtained. Subsequently, the trained model 2009 is then used to predict the outcome for cases in the validation data set 2005, the so called "unseen data" (from the perspective of the trained model). Because the real outcome of each case in the validation data set is known, at this point a validation report can be generated comparing the predicted results with the actual results and the findings can be used to determine the validity of the trained model, essentially whether it is successfully predicting the actual outcomes for the cases in the validation data set. The end result is an assessment of how well the trained system model performs on unseen data.

Using the Trained NNM

The controller conducts pre-processing of input attributes of patient admissions (transactions). The input attributes can be, in this overly simplified example: primary patient diagnosis, identity and specialties of admitting provider and admitting team members, identity and specialties of consulting providers and consulting team members, identity of nurses, ward to which patient is admitted, presence, frequency, date of, and content (and objective quantitative scoring) of handoff documentation filed by admitting team, consulting team, nurses and other personnel during admission, quantity of handoffs by admitting team, consulting team, nurses and other personnel completed during admission, handoff training completion dates of treating admitting providers, consulting providers, and nurses, treating admitting providers, consulting providers, and nurses, handoff evaluation dates and scores for treating admitting providers, consulting providers, and nurses, handoff workflow data capture, audio or video data captured from verbal handoff discussions, and other hospital information system data, documentation, and clinical charting, as mentioned above. The controller generates an output value of the trained NNM based upon the input attributes of the new clinical patient admission transaction. The output value can be a predicted risk of medical error and/or adverse event and predicted rate of medical errors and/or adverse events per X admissions (or per X admissions with Y primary diagnosis) for a given hospital ward. Finally, the server device can compare the predicted risk of a medical error and/or adverse event or ward medical error and/or adverse event rate with a threshold criteria or business logic to determine whether notification or escalation is required.

Unsupervised Learning

Figure 29:
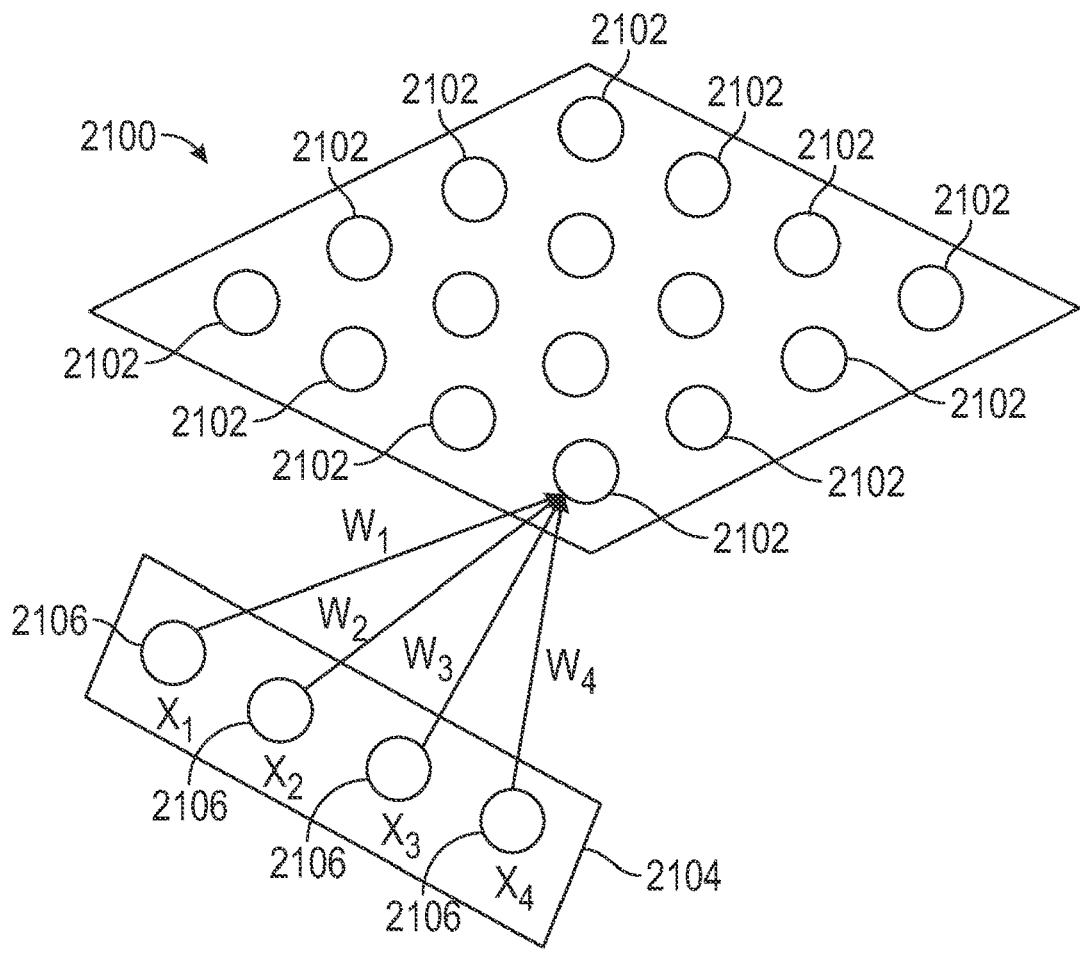
FIGS. 29-30 are illustrations of an exemplary Self-Organizing Map (SOM) and the input data set to the SOM network.
Figure 30:
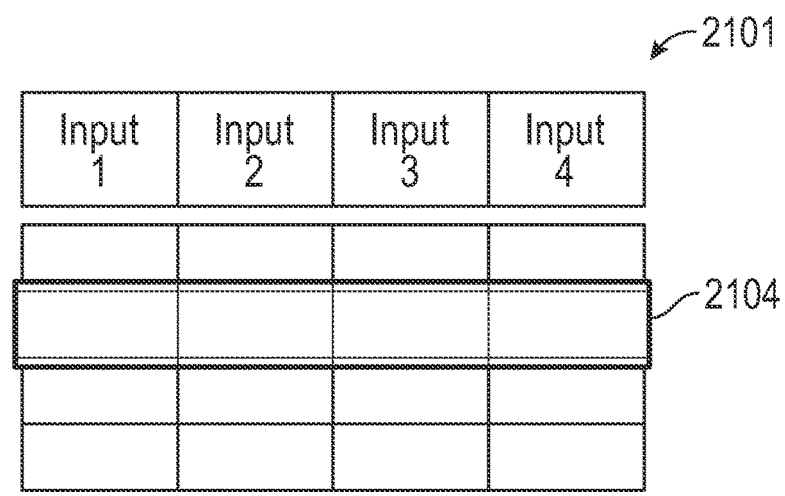
Figure 31:
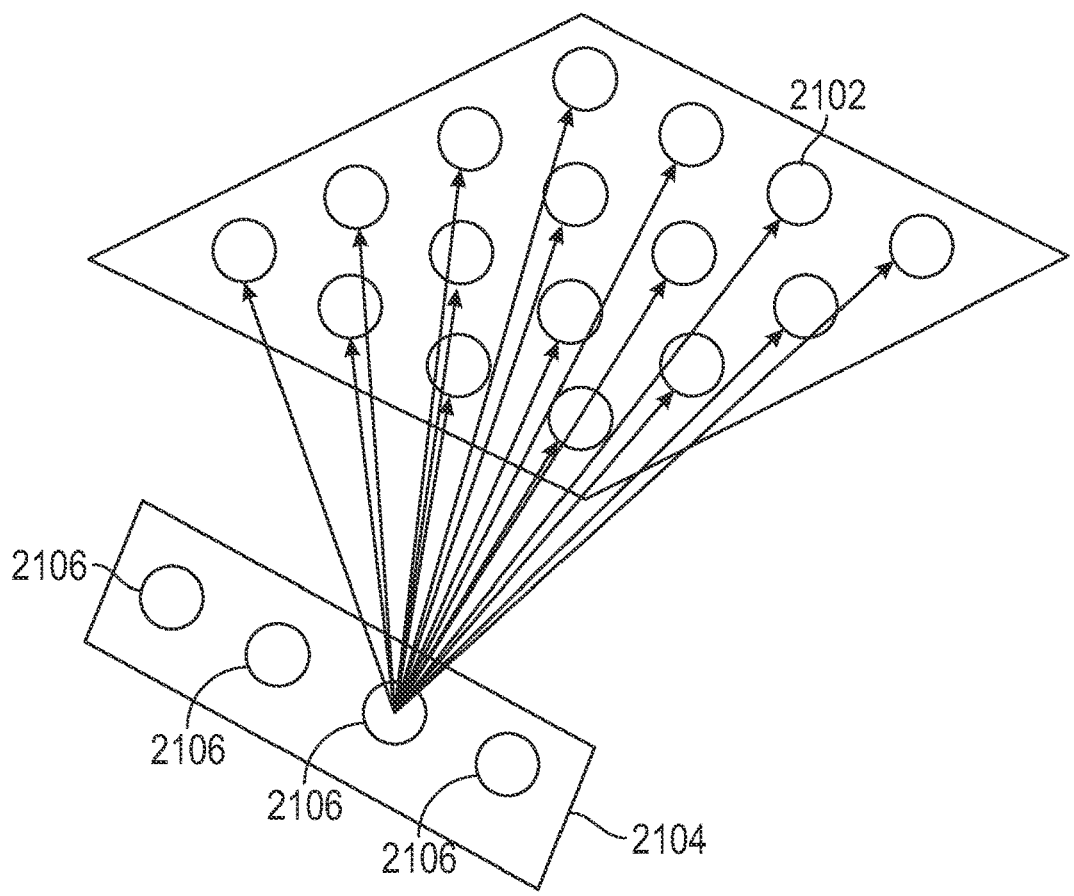
FIG. 31 is an illustration of how each node of the SOM network will contain the connection weights of the connections to all connected input nodes.
Figure 32:
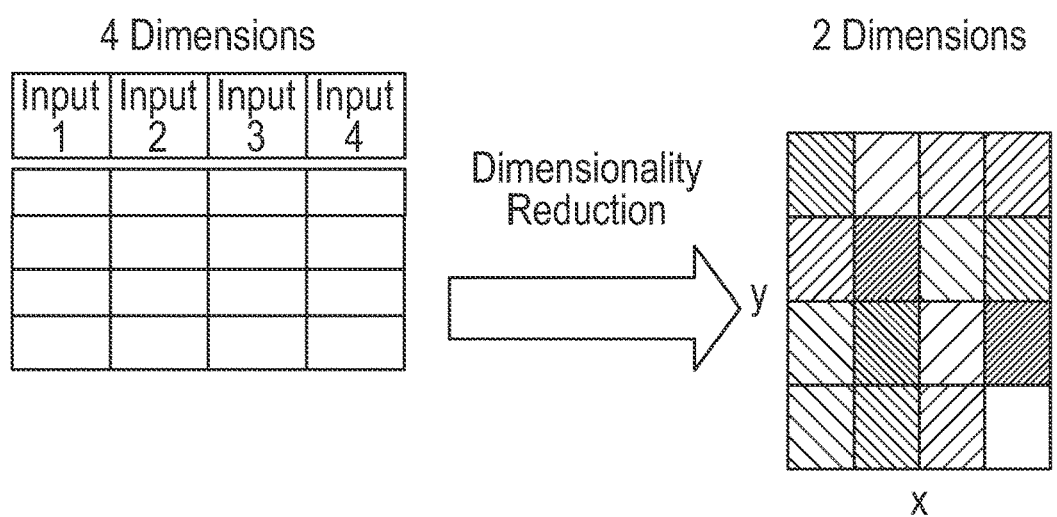
FIG. 32 is an illustration of the SOM network used to reduce dimensionality of the input data sets.

The server can also use unsupervised learning techniques as well as supervised learning techniques to determine the group or cluster to which particular patient events belong. Referring to FIGS. 29-31, a Self-Organizing Map (SOM) 2100 is an unsupervised neural network that consists of a grid or lattice of nodes 2102 with a certain structure which may be one, two or three dimensional. The SOM 2100 includes a grid of nodes 2102 on some two (or three) dimensional plane where each node has an x and y coordinate (and z coordinate in the case of a three-dimensional node network), a so called fixed topological position, and an input layer 2104 with various input nodes 2106 that are used to provide input to the SOM network 2100. The input layer 2104 can be a random row from the training data set 2101 (FIG. 30). The specific number of inputs is dependent on the specifics of the data set. Each input node is connected to every node of the two (or three) dimensional SOM network (FIG. 31) and each connection has a synaptic connection weight (w), much like that in supervised networks. Each node 2102 of the SOM network 2100 will contain the connection weights of the connections to all connected input nodes. As partially shown in FIG. 31, each SOM network node 2102 is connected to all input nodes 2106, thus each node of the SOM network will have an equivalent number of connection weights (equivalent to the number of input nodes).

Figure 33:
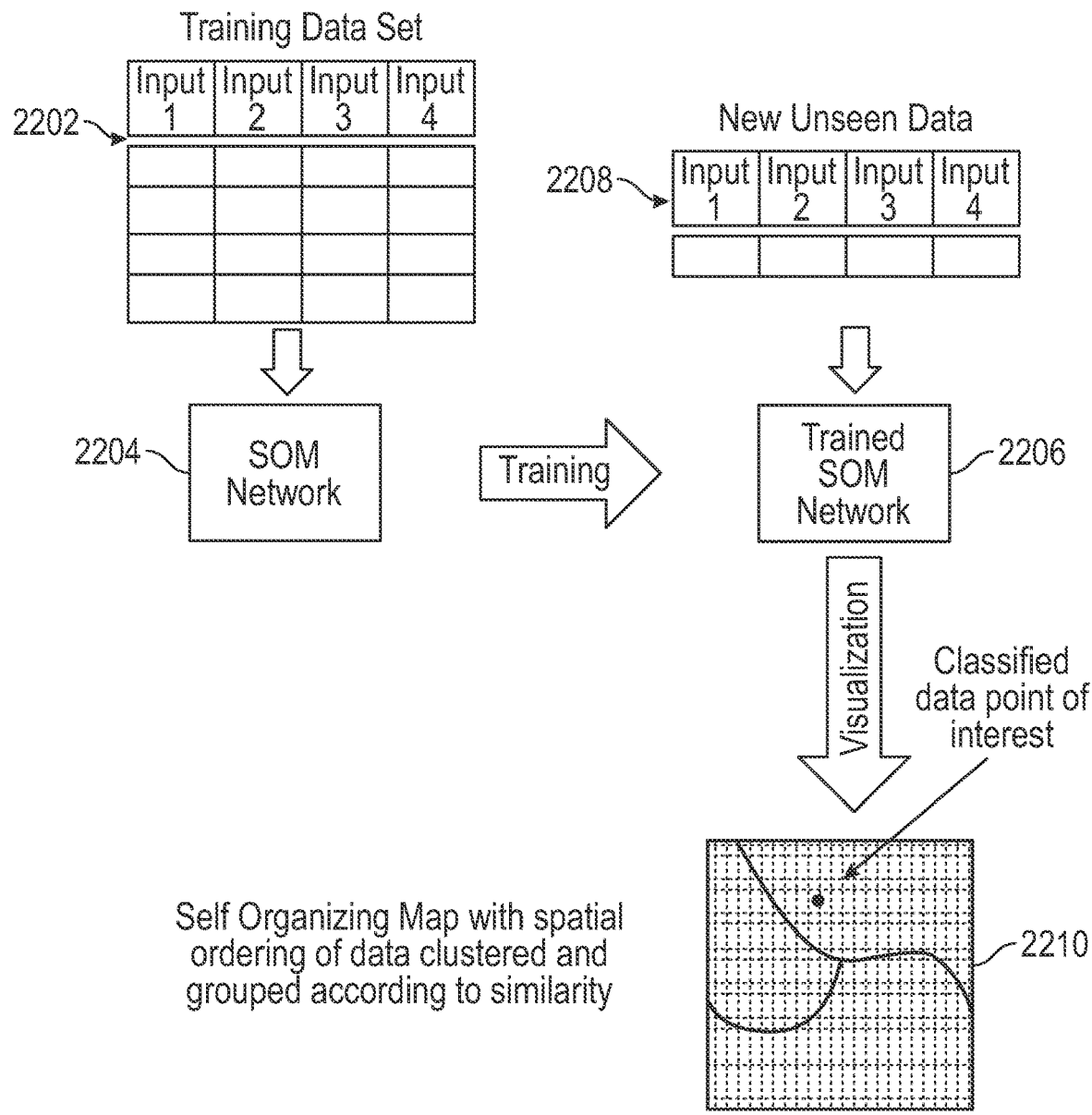
FIG. 33 is a block diagram illustrating high level operations of the process for training the SOM.

A representation of the process for creating, training and using the trained model is shown in FIG. 33. A training data set includes a plurality of patient attributes of past patient events. The training data set 2202 is input into the SOM network 2204. The SOM network 2204 is trained to generate the trained SOM network 2206. New data 2208 is input into the trained SOM network 2206. The output of the trained SOM network can be an SOM image 2210 that shows spatial ordering of data clustered and grouped according to similarity such that that the group or cluster to which a given data point of interest belongs can be determined. As discussed later, the SOM image 2210 can be rendered on a client device.

Figure 34:
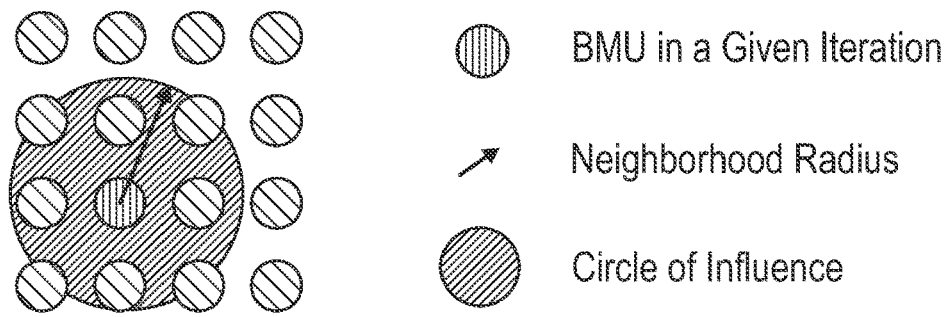
FIG. 34 is an illustration of the process for training the SOM network.

Referring to FIG. 34, the first step in SOM model training is to initialize values of the plurality of synaptic connection weights to random values. The next step is to randomly select one row (one past patient event) from the training data set, which is most typically normalized (for this purpose) and determine which of the plurality of network nodes is the best matching unit (BMU) according to a discriminant function such as a Euclidean Distance. When a node is selected and compared with the row selected from the training data, the Euclidean Distance which serves as our discriminant function for this competitive network, is calculated, though others, for example, Manhattan distance, can be used. This process is repeated for each SOM node. The SOM node with the smallest Euclidean distance (or said another way, the neuron whose weight vector comes closest to the input vector) will be designated as the BMU for that randomly picked input data row. Thus, the BMU is the closest SOM network node to the randomly picked input data row. Next, the neighborhood radius, or the so called neighborhood kernel (function), is calculated. Usually the Gaussian function is used, although the Bubble function is another possibility. The neighborhood radius allows for the determination of the specific BMU neighborhood nodes in the SOM network to which connection weight updates should be applied on the next training iteration. All nodes within the "circle of influence" corresponding to the neighborhood radius are updated. The procedure used to calculate this radius value is shown below:

$$r(n)=r_0 e-(n)/\lambda$$

$r_0$=initial radius
n=iteration number
$\lambda$=time constant

Usually a large initial radius value is selected for the purpose of having almost the entire network covered. n is the iteration number and lambda is a time constant (iteration limit). This calculation of the radius is basically a decreasing function whereby the value of r will diminish over the course of the training iterations, another way of saying the topological neighborhood decays with distance or that the topological neighborhood decreases monotonically over the period of iterations. Hence a greater number of SOM nodes are updated early in the training process, and on subsequent rounds there is a smaller number of nodes in the neighborhood of the BMU that get updated. At this point in the training process the connection weights are updated for the BMU and those nodes in the neighborhood of influence. The connection weight update equation is as follows:

$$W_k(n+1)=W_k(n)+\alpha(n)h_{ck}(n)[x(n)-W_k(n)]$$

Where n is the iteration number, k is the index of the node in the SOM network, and $W_k(n+1)$, is the updated connection weight (weight vector of node k) for the next training iteration which is calculated as shown using $\alpha(n)$, a monotonically decreasing learning coefficient (learning rate), $h_{ck}(n)$, the neighborhood kernel (function)—something that, for simplicity can be called the influence factor, and $[x(n)-W_k(n)]$, the difference between $W_k(n)$, the old weights (the weights on the current training iteration), and x(n), a randomly selected row or input pattern from the input data that was used on the current iteration.

Thus, a simplistic way of stating this is the new weights for the next training iteration are calculated by adding the old weights from the current training iteration to the product of the learning rate multiplied by the influence factor multiplied by the difference or delta between the old weights and the randomly picked input data used for a given training iteration. Note the influence factor is often a radial based function such as the Gaussian function (though as mentioned earlier, other types of radial functions can also be used) and this is the reason why the nodes closest to the BMU have or receive more influence than those further away from the BMU which are updated by a smaller amount. Also, in regards to the learning rate, it decreases (decays) over time, meaning that in the earlier phases of the training process, there is more learning, but over the training period the learning effect will decrease in each sequential iteration. The delta between the old weights and the randomly picked input data used in a given training iteration is a determinant of how different the current SOM network node is in comparison with the randomly picked input data row used on the given training iteration. Hence, these three factors are the determinants of the updated connection weights that should be used on each subsequent training iteration for the SOM network nodes. The learning rate and the influence factor decay over the period of iteration to allow for the proper convergence of the solution such that a stable result can be obtained at the end of training. The training process is repeated for a fixed number of N iterations to generate the trained SOM network.

Returning to FIG. 15, an exemplary data set includes a plurality of data [1, 2 . . . N], and a number of properties [1, 2 . . . N] for each data. The data set can be a plurality of past patient events and the properties can be a number of attributes of each past patient event. The high dimensionality of the data sets can make visualization of the data difficult. As illustrated in FIG. 33, the dimensionality reduction aspect of SOM networks allows data of high dimensionality to be projected to a two-dimensional grid which expresses the similarity of samples and the distance between them. However, the mere position on the map cannot sufficiently embody the complexity of an n-dimensional vector. The challenge of information representation is a mature area of research and numerous approaches of displaying multidimensional multivariate data have been proposed as discussed in the article entitled "30 Years of Multidimensional Multivariate Visualization" authored by Wong and Bergeron (1997), the contents of which are hereby incorporated by reference. One such technique therein described utilized by the system is Scalable Vector Graphics (SVG), an XML markup language for describing two-dimensional vector graphics, both static and animated.

Figure 35:
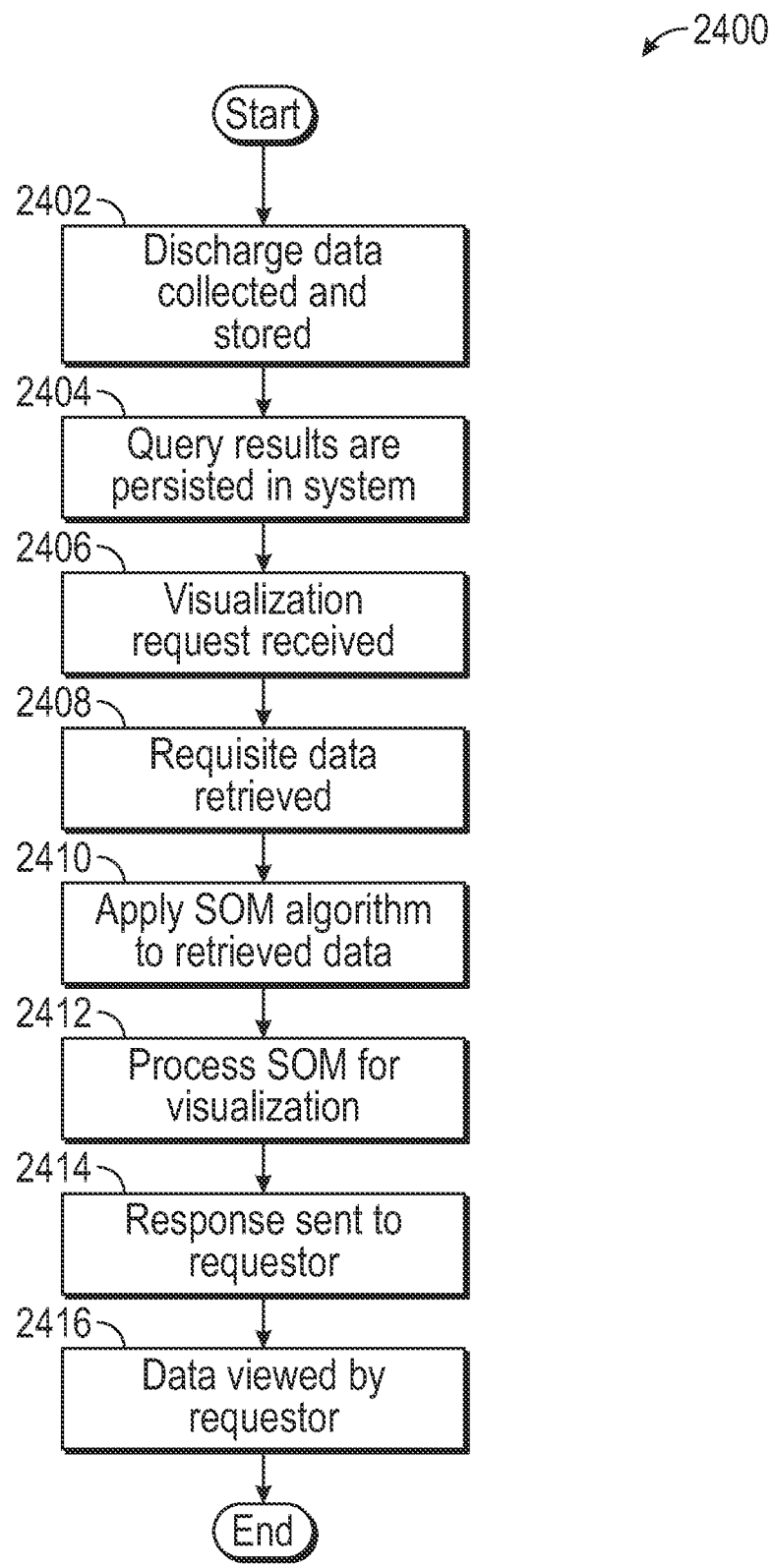
FIG. 35 is a flow diagram illustrating exemplary operations of the system to generate the graphical image including the visualization.

Referring to FIG. 35, an exemplary process 2400 by which the system can employ an SOM network to take a data set of events defined by n-dimensional input attributes and generate a visualization of the results after passing the data into the SOM network will be discussed. At 2402, input data is collected and stored. For example, the DCE collects location data of the patient from the RFID tags as discussed above and transmits it to the backend devices. This data can be stored in the database at the server with respect to the patient as discussed above. At 2404, the server can maintain query results in the memory. At 2406, the server receives a visualization request from a client device or web browser via the network with query parameters. At 2408, the server sends a data request with the query parameters to the backend device, which retrieves from the database the data sets consistent with the request. At 2410, the backend device inputs the data sets to the trained SOM network. At 2412, the backend device generates a visualization or graphical image based upon the output from the SOM network. At 2414, the backend device sends the graphical image to the server, which either sends it to the client device and/or renders the image on a display of a website. The output produced can be groupings or clustering of discharges with similar characteristics, much like the classical "market segmentation" or "document classification" tasks for which SOMs are widely employed. This SOM output can be generated from a variety of vantage points or perspectives with one or more specified criteria, for example, specific occupations, or for only veterans, or only for a particular subset of patients processed by a particular employee, a group of employees, a service line, a group of service lines, a hospital facility or a group of hospital facilities in a given region, to name a few examples. SOM techniques can also be employed to predict the classification, type, or grouping of adverse events leveraging the attributes or inputs from already existing data sets.

Exemplary Implementation

Figure 36:
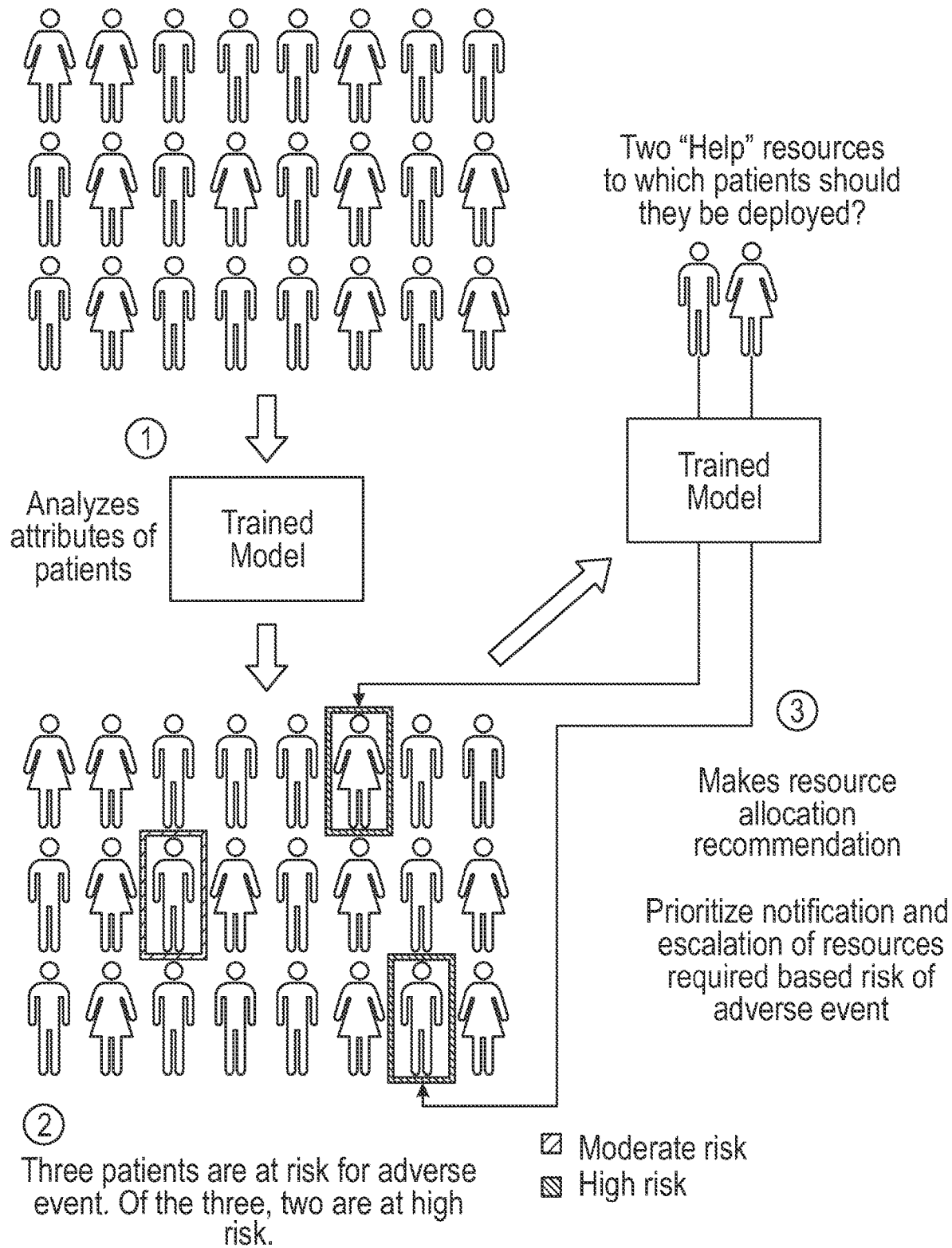
FIG. 36 is an illustration of an exemplary use case in which the trained model determines an adverse event risk for a plurality of patient events and to which patient should help resources be deployed.

Referring to FIG. 36, an exemplary implementation will be discussed for a case in which an NNM is created, trained and validated to determine whether an adverse event is likely to occur for a given patient. The backend devices (one or more server devices) use NNMs to predict which patients are at risk for an adverse event and to determine to which patients, if any, should more resources be allocated (i.e. the backend devices can determine whether there is an opportunity, or more specifically, a high probability, of successfully mitigating the likelihood of a given predicted adverse event by allocating additional resource(s)).

In the example shown in FIG. 36, there are 24 patients that are being treated by a care group. The controller of the server utilizes a trained NNM that takes inputs as shown at 1 and determines an adverse event risk category (moderate or significant risk) of the patient. The inputs can be attributes of the patient, such as handover number, interval between handover, doctor(s) treating patient, facility location, attributes of facility resources (for example, the available help resources' expertise and past performance on handovers with similar patients), etc.

In doing so, the server can determine whether (the probability that) deployment of any given available resource(s) is likely to mitigate the predicted adverse event risk for a given patient event; moreover, the server's NNMs can predict the probability of an adverse event occurring that would potentially be reduced if a given resource allocation recommendation is made. As shown at 2, three patients are at risk for an adverse event with two being high risk and one being a moderate risk. Based on business logic and these results, the server may determine it does or does not recommend that any of the available additional resources be deployed as shown at 3. There are a number of approaches the server could take to arrive at a decision to recommend or not recommend the deployment of any available resource(s). One demonstrative approach the server might take would be to recommend the deployment of an available resource if the probability weighted reduction in the risk of an adverse event exceeded a particular threshold. If more than one potential allocation of available resources might be feasible at any given time, the business logic of the server, for example, could be configured such that the server issues the recommendation that in the net (summed together) results in the largest probability weighted reduction for the hospital system as a whole at that moment—i.e. the constellation of recommendations at that moment that collectively has the maximum potential beneficial impact (probability weighted suicide reduction) for the hospital in question. Those skilled in the art know there is a broad set of approaches that the system may take to make such recommendations and the approaches can further vary depending on the specific optimization objective(s). Moreover, while in practice the optimization technique employed may be more complex, the embodiment herein was selected to provide a simple demonstrative example of one of many potential optimization approaches the system might take. The resource allocation example herein is not intended to limit the scope of potential approaches to that described.

Below is a non-exhaustive list of adverse events the server can determine.

Surgical Events
 A. Surgery performed on the wrong body part
 B. Surgery performed on the wrong patient
 C. Wrong surgical procedure performed on a patient
 D. Unintended retention of foreign object in a patient after surgery or procedure
 E. Intraoperative or immediately postoperative death Product or Device Events
 A. Patient death or serious disability associated with use of contaminated drugs, devices, or biologics provided by the health care facility
 B. Patient death or serious disability associated with use or function of a device in patient care in which the device is used or functions other than as intended
 C. Patient death or serious disability associated with intravascular air embolism that occurs while being cared for in a health care facility Patient Protection Events
 A. Infant discharged to the wrong person
 B. Patient death or serious disability associated with patient elopement
 C. Patient suicide, or attempted suicide resulting in serious disability, while being cared for in a health care facility Care Management Events
 A. Patient death or serious disability associated with a medication error
 B. Patient death or serious disability associated with a hemolytic reaction because of administration of incompatible blood or blood products
 C. Maternal death or serious disability associated with labor or delivery in a low-risk pregnancy while cared for in a health care facility
 D. Patient death or serious disability associated with hypoglycemia, the onset of which occurs while patient is being cared for in a health care facility
 E. Death or serious disability associated with failure to identify and treat hyperbilirubinemia in neonates
 F. Stage III or Stage IV pressure ulcers acquired after admission to a health care facility
 G. Patient death or serious disability because of spinal manipulative therapy
 H. Artificial insemination with the wrong donor sperm or wrong egg Environmental Events
 A. Patient death or serious disability associated with an electric shock while being cared for in a health care facility
 B. Any incident in which a line designated for oxygen or other gas to be delivered to a patient contains the wrong gas or is contaminated by toxic substances
 C. Patient death or serious disability associated with a burn incurred from any source while being cared for in a health care facility D. Patient death or serious disability associated with a fall while being cared for in a health care facility E. Patient death or serious disability associated with the use of restraints or bedrails while being cared for in a health care facility Criminal Events A. Care provided by someone impersonating a health care provider B. Abduction of a patient of any age C. Sexual assault on a patient within or on the grounds of a health care facility D. Death or significant injury resulting from a physical assault that occurs within or on the grounds of the facility Condition Events 1. Foreign object retained after surgery
   2. Air embolism
   3. Blood incompatibility
   4. Pressure ulcers (stages III and IV)
   5. Falls
      A. Fracture
      B. Dislocation
      C. Intracranial injury
      D. Crushing injury
      E. Burn
      F. Electric shock
   6. Manifestations of poor glycemic control
      A. Hypoglycemic coma
      B. Diabetic ketoacidosis
      C. Nonkeototic hyperosmolar coma
      D. Secondary diabetes with ketoacidosis
      E. Secondary diabetes with hyperosmolarity
   7. Catheter-associated urinary tract infection
   8. Vascular catheter-associated infection
   9. Deep vein thrombosis/pulmonary embolism associated with the following
      A. Total knee replacement
      B. Hip replacement
   10. Surgical site infection
      A. Mediastinitis after coronary artery bypass graft
      B. Associated with certain orthopedic procedures involving the
         a. Spine
         b. Neck
         c. Shoulder
         d. Elbow
      C. Associated with certain bariatric surgical procedures for obesity
         a. Laparoscopic gastric bypass
         b. Gastroenterostomy
         c. Laparoscopic gastric restrictive surgery Therefore, the present disclosure concerns machine learning models, the disclosure's application of specific technical techniques that leverage the specific aspects or attributes of particular care episodes in hospital systems in conjunction with the other system components that permit the identification of the an adverse event risk.

While only certain features of the invention have been illustrated and described herein, many modifications and changes will occur to those of ordinary skill in the art. The following claims are intended to cover all such modifications and changes.

What is claimed is:

1. A method for predicting an outcome associated with a new event, the method comprising:
storing a plurality of past events, each of the plurality of past events including a plurality of patient attributes and a quantifiable outcome;
training a neural network model (NNM) to generate a trained model, wherein the training of the NNM includes:
performing pre-processing on a plurality of patient attributes for each of the plurality of past events to generate a plurality of past input data sets;
dividing the plurality of past events into a first set of training data and a second set of validation data;
iteratively performing a machine learning algorithm (MLA) to update synaptic weights of the NNM based upon the first set of training data; and
validating the NNM based upon the second set of validation data;
receiving a plurality of input attributes of the new event;
performing pre-processing on the plurality of input attributes to generate an input data set;
generating an output value from the trained model based upon the input data set; and
classifying the output value into an adverse event category to predict an outcome,
wherein one or more of the plurality of input attributes of the new event includes handover metrics of a facility associated with the new event, the handover metrics including intervals between handovers and patient current and prior locations during a given interval between handovers.

2. The method of claim 1, wherein one or more of the plurality of input attributes of the new event includes data from an RFID tag and a hospital information system.

3. The method of claim 1, wherein the new event is a patient being treated by a doctor associated with a facility, the method further comprising:
associating the output value of the event with the facility;
predicting an outcome of the facility by tracking a plurality of output values for different events associated with the facility.

4. The method of claim 3, wherein the output value of each event is a probability of an adverse event, the method further comprises determining the output value continuously at predetermined time periods to determine when a rate of increase of the probability of the adverse event output values is greater than a predetermined threshold.

5. The method of claim 1, wherein the receiving of the plurality of input attributes of the new event further includes receiving one or more messages including a patient identification and location information associated with a first RFID tag and a medical professional identification and location information associated with a second RFID tag from a data collection engine (DCE).

6. The method of claim 1, further comprising:
alerting and assigning an allocation of appropriate clinical resources to a patient based upon an optimization algorithm in accordance with the adverse event category of the new event and attributes of available clinical resources.

7. The method of claim 1, wherein one or more of the plurality of input attributes of the new event includes a quality rating of handoff documentation associated with each of the handovers.

8. A method for predicting an outcome associated with a new event, the method comprising:
training a Self-Organizing Map (SOM) to generate a trained model, wherein the trained model includes a plurality of network nodes arranged in a grid or lattice and in fixed topological positions, an input layer with a plurality of input nodes representing input attributes of past patient events, wherein each of the plurality of input nodes is connected to all of the plurality of network nodes by a plurality of synaptic weights; and wherein the training of the SOM includes:

initializing values of the plurality of synaptic weights to random values, randomly selecting one past patient event and determining which of the plurality of network nodes is a best matching unit (BMU) according to a discriminant function, wherein the discriminant function is a Euclidean Distance; and iteratively calculating a neighborhood radius associated with the BMU to determine neighboring network nodes for updating, and updating values of synoptic weights for neighboring network nodes within the calculated neighborhood radius for a fixed number of iterations to generate the trained model;

receiving a plurality of input attributes of the new event;

performing pre-processing on the plurality of input attributes to generate an input data set;

generating an output value from the trained model based upon the input data set; and classifying the output value into an adverse event category to predict an outcome, wherein:

one or more of the plurality of input attributes of the new event includes handover related data;

the receiving of the plurality of input attributes of the new event further comprises receiving a plurality of new events, each including a plurality of input attributes;

the generating of the output value and classifying the output value further includes generating a graphical image including input attributes for each of the plurality of new events;

the method further comprises receiving a graphical display request from a remote client device and transmitting the graphical image to the remote client device as a response; and the graphical image is a cluster diagram including a plurality of clusters of new events having one or more of same input attributes.

9. The method of claim 8, wherein one or more of the plurality of input attributes of the new event includes handovers and a quality rating of handoff documentation associated with each of the handovers.

10. A method for predicting an outcome associated with a new event, the method comprising:

training a neural network model (NNM) model to generate a trained model based upon a plurality of past events, each of the plurality of past events including a plurality of input attributes and a quantifiable outcome;

wherein the training of the NNM model includes:

performing pre-processing on a plurality of patient attributes for each of the plurality of past events to generate a plurality of past input data sets;

dividing the plurality of past events into a first set of training data and a second set of validation data;

iteratively performing a machine learning algorithm (MLA) to update synaptic weights of the NNM based upon the first set of training data; and validating the NNM based upon the second set of validation data;

receiving a plurality of input attributes of the new event;

performing pre-processing on the plurality of input attributes of the new event to generate an input data set;

generating an output value from the trained model based upon the input data set; and classifying the output value into an adverse event category to predict an outcome, wherein one or more of the plurality of input attributes of the new event includes handovers, intervals between handovers, and a quality rating of handoff documentation associated with each of the handovers.

11. The method of claim 10, wherein the intervals between handovers are further handovers from a first healthcare provider to a second healthcare provider, wherein the second healthcare provider is external from the first healthcare provider and not inter-hospital with the first healthcare provider.

12. The method of claim 10, wherein the receiving of the plurality of input attributes of the new event further includes receiving one or more messages including a patient identification and location information associated with a first RFID tag and a medical professional identification and location information associated with a second RFID tag from a data collection engine (DCE).

* * * * *